US010828358B2

(12) United States Patent
Kruse et al.

(10) Patent No.: US 10,828,358 B2
(45) Date of Patent: Nov. 10, 2020

(54) HELICOBACTER PYLORI VACCINES

(71) Applicants: TECHNISCHE UNIVERSITÄT MÜNCHEN, Munich (DE); MAX-PLANCK-GESELLSCHAFT ZUR FÖRDERUNG DER WISSENSCHAFTEN E.V., Munich (DE)

(72) Inventors: Tobias Kruse, Munich (DE); Daniel Hornburg, Munich (DE); Markus Gerhard, Munich (DE); Matthias Mann, Stockdorf (DE); Felix Meissner, Gauting (DE)

(73) Assignees: TECHNISCHE UNIVERSITÄT MÜNCHEN, Munich (DE); MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 52 days.

(21) Appl. No.: 16/061,938

(22) PCT Filed: Dec. 14, 2016

(86) PCT No.: PCT/EP2016/080878
§ 371 (c)(1),
(2) Date: Jun. 13, 2018

(87) PCT Pub. No.: WO2017/102779
PCT Pub. Date: Jun. 22, 2017

(65) Prior Publication Data
US 2018/0360941 A1    Dec. 20, 2018

(30) Foreign Application Priority Data

Dec. 14, 2015 (EP) ..................................... 15199862

(51) Int. Cl.
| | |
|---|---|
| A61K 39/02 | (2006.01) |
| A61P 1/04 | (2006.01) |
| A61P 35/00 | (2006.01) |
| C07K 14/205 | (2006.01) |
| A61K 39/00 | (2006.01) |
| G01N 33/569 | (2006.01) |

(52) U.S. Cl.
CPC ........ *A61K 39/0208* (2013.01); *A61K 39/105* (2013.01); *A61P 1/04* (2018.01); *A61P 35/00* (2018.01); *C07K 14/205* (2013.01); *A61K 2039/55544* (2013.01); *A61K 2039/70* (2013.01); *G01N 33/56922* (2013.01)

(58) Field of Classification Search
None
See application file for complete search history.

(56) References Cited

U.S. PATENT DOCUMENTS

| | | | |
|---|---|---|---|
| 6,025,164 A | 2/2000 | Bolin et al. | |
| 6,838,089 B1 | 1/2005 | Carlsson et al. | |
| 2002/0151462 A1 | 10/2002 | Lissolo | |
| 2004/0033240 A1 | 2/2004 | Guy et al. | |
| 2005/0063987 A1 | 3/2005 | Knapp et al. | |
| 2005/0175629 A1 | 8/2005 | Del Giudice | |
| 2006/0193866 A1 | 8/2006 | Meinke et al. | |
| 2007/0026018 A1 | 2/2007 | Ellis et al. | |
| 2014/0112948 A1 | 4/2014 | Wang | |

FOREIGN PATENT DOCUMENTS

| | | |
|---|---|---|
| EP | 1508572 | 2/2005 |
| EP | 2082750 | 7/2009 |
| WO | WO 98/22135 A1 | 5/1998 |
| WO | WO 98/24475 A1 | 6/1998 |
| WO | WO 98/43478 A1 | 10/1998 |
| WO | WO 00/22135 A1 | 4/2000 |
| WO | WO 2001/083531 | 11/2001 |
| WO | WO 2001/083533 | 11/2001 |
| WO | WO 2002/002141 | 1/2002 |
| WO | WO 2002/066501 | 8/2002 |
| WO | WO 2004/094467 A2 | 11/2004 |
| WO | WO 2011/018779 | 2/2011 |
| WO | WO 2011/081598 | 7/2011 |
| WO | WO 2012/031530 | 3/2012 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Haj et al., http//dx.doi.org/10.5772/63826, pp. 141-164.*
Montalban, Gut, 49:584-584, 2001.*
Extended European Search Report, EP 15199862.2, dated Sep. 19, 2016, 12 pages.
International Search Report and Written Opinion, PCT/EP2016/080878, dated May 15, 2017, 23 pages.
International Preliminary Report on Patentability, PCT/EP2016/080878, dated Jun. 28, 2018, 12 pages.
Blaser et al., "Infection with Helicobacter pylori strains possessing cagA is associated with an increased risk of developing adenocarcinoma of the stomach," Cancer Research 55(10):2111-2115, 1995.
Doro et al., "Surfome analysis as a fast track to vaccine discovery," Molecular & Cellular Proteomics 8.7:1728-1737, 2009.
Finco et al., "Approach to discover T- and B-cell antigens of intracellular pathogens applied to the design of Chlamydia trachomatis vaccines," PNAS 108(24):9969-9974, Jun. 14, 2011.
Forman, "Helicobacter pylori and gastric cancer," Scandinavian Journal of Gastroenterology 31:sup214, 31-33, 1996.

(Continued)

*Primary Examiner* — Brian Gangle
(74) *Attorney, Agent, or Firm* — Leydig, Voit & Mayer, Ltd.

(57) ABSTRACT

The present invention relates to immunogenic compositions and their use in the prevention or treatment of diseases or disorders caused by or associated with *Helicobacter pylori*, in particular *H. pylori* infection and gastroduodenal disorders caused by *H. pylori*. The present invention further relates to methods of detecting *H. pylori* infection in a subject.

17 Claims, 7 Drawing Sheets

Specification includes a Sequence Listing.

(56) References Cited

OTHER PUBLICATIONS

Gao et al., "The evolution of Helicobacter pylori antibiotics resistance over 10 years in Beijing, China," Helicobacter 15(5):460-466, 2010.

Gómez-Gascón et al., "Exploring the pan-surfome of *Streptococcus suis*: Looking for common protein antigens," J Proteomics, 13 pages, 2012.

Graham et al. "The time to eradicate gastric cancer is now," Gut 54(6):735-738, 2005.

Jemal et al., "Global cancer statistics," CA Cancer J Clin 61(2):69-90, 2011.

Moffitt et al., "$T_H17$-based vaccine design for prevention of *Streptococcus pneumoniae* colonization," Cell Host & Microbe 9(2):158-165, Feb. 17, 2011.

Nomura et al., "Helicobacter pylori infection and the risk for duodenal and gastric ulceration," Annals of Internal Medicine 120(12):977-981, Jun. 15, 1994.

Parsonnet et al., "Helicobacter pylori infection and the risk of gastric carcinoma," New England Journal of Medicine 325(16):1127-1131, 1991.

Perez-Perez et al., "Epidemology of helicobacter pylori infection," Helicobacter 9 Supp. 1:1-6, 2004.

Rodríguez-Ortega et al., "Characterization and identification of vaccine candidate proteins through analysis of the group A Streptococcus surface proteome," Nature Biotechnology 24(2):191-197, Feb. 2006.

Shiota et al., "Population-based strategies for Helicobacter pylori-associated disease management: a Japanese perspective," Expert Rev Gastroenterol Hepatol. 4(2):49-156, Apr. 2010.

Takeuchi et al., Abnormal gastroesophageal flap valve is highly associated with endoscopic reflux esophagitis after helicobacter pylori eradication,: Helicobacter 9(1):1-8, 2004.

United States Centers for Disease Control and Prevention, "A CDC framework for preventing infectious diseases. Sustaining the essentials and innovating for the future," Oct. 2011, Atlanta Georgia, 33 pages.

\* cited by examiner

SEQUENCE LISTING

```
<160> NUMBER OF SEQ ID NOS: 29

<210> SEQ ID NO 1
<211> LENGTH: 201
<212> TYPE: PRT
<213> ORGANISM: Helicobacter pylori

<400> SEQUENCE: 1

Met Arg Leu His Thr Ala Phe Phe Gly Ile Asn Ser Leu Leu Val Ala
1               5                   10                  15

Thr Leu Leu Ile Ser Gly Cys Ser Leu Phe Lys Lys Arg Asn Thr Asn
            20                  25                  30

Ala Gln Leu Ile Pro Pro Ser Ala Asn Gly Leu Gln Ala Pro Ile Tyr
        35                  40                  45

Pro Pro Thr Asn Phe Thr Pro Arg Lys Ser Ile Gln Pro Leu Pro Ser
    50                  55                  60

Pro Arg Leu Glu Asn Asn Asp Gln Pro Ile Ile Ser Ser Asn Pro Thr
65                  70                  75                  80

Asn Ala Ile Pro Asn Thr Pro Ile Leu Thr Pro Asn Asn Val Ile Glu
                85                  90                  95

Leu Asn Ala Val Gly Met Gly Val Ala Pro Glu Ser Thr Ile Ser Pro
            100                 105                 110

Ser Gln Ala Leu Ala Leu Ala Lys Arg Ala Ala Ile Val Asp Gly Tyr
        115                 120                 125

Arg Gln Leu Gly Glu Lys Met Tyr Gly Ile Arg Val Asn Ala Gln Asp
    130                 135                 140

Thr Val Lys Asp Met Val Leu Gln Asn Ser Val Ile Lys Thr Arg Val
145                 150                 155                 160

Asn Ala Leu Ile Arg Asn Ala Glu Ile Thr Glu Thr Ile Tyr Lys Asp
                165                 170                 175

Gly Leu Cys Gln Val Ser Met Glu Leu Lys Leu Asp Gly Arg Ile Trp
            180                 185                 190

Tyr Arg Ile Leu Ser Gly Ser Arg Gly
        195                 200

<210> SEQ ID NO 2
<211> LENGTH: 285
<212> TYPE: PRT
<213> ORGANISM: Helicobacter pylori

<400> SEQUENCE: 2

Met Lys Arg Ile Leu Phe Phe Leu Ala Ala Thr Thr Phe Leu Leu Arg
1               5                   10                  15

Ala Glu Thr Ala Ser Ala Thr Ile Asn Thr Thr Val Asp Pro Asn Val
            20                  25                  30
```

```
Met Phe Ser Glu Ser Ser Thr Gly Asn Val Lys Lys Asp Arg Lys Arg
            35                  40                  45

Val Leu Lys Ser Met Val Asp Leu Glu Lys Glu Arg Val Lys Asn Phe
 50                  55                  60

Asn Gln Tyr Ser Glu Thr Lys Met Ser Lys Gly Asp Leu Ser Ala Phe
 65                  70                  75                  80

Gly Ala Phe Phe Lys Gly Ser Leu Glu Asp Cys Val Glu Gln Lys Ile
                 85                  90                  95

Cys Tyr Tyr Glu His Arg Asn Gly Lys Val Ser Phe Val Val Asn Asp
                100                 105                 110

Arg Glu Lys Phe Tyr Lys His Val Leu Lys Asp Leu Gly Thr Glu Leu
            115                 120                 125

Ser Leu Pro Leu Phe Asn Trp Leu Tyr Lys Gly Ser Asp Phe Gly Ala
130                 135                 140

Leu His Glu Gln Phe Gly Asp Met Tyr Asp Gly Tyr Ile Lys Tyr Leu
145                 150                 155                 160

Ile Ser Met Val Arg Val Ser Gln Lys Glu Lys Ala Arg Lys Val Asp
                165                 170                 175

Ala Ile Val Leu Lys Lys Met Glu Glu Gln Ala Glu Lys Asp Thr Lys
            180                 185                 190

Ala Ala Phe Gln Lys Arg Ser Ser Gly Glu Leu Glu Ser His Thr Asp
            195                 200                 205

Ser Pro Glu Phe Ile Ser Ser Lys Thr Gln Asn Ser Ser Asn Pro
210                 215                 220

Asp Leu Asp Pro Met Thr Asn Ala Asn Thr Leu Lys Glu Thr Ala Ser
225                 230                 235                 240

Lys Glu Pro Glu Thr Ser Ser Lys Lys Glu Lys Lys Pro Lys Lys Lys
                245                 250                 255

Arg Arg Leu Ser Lys Lys Glu Lys Gln Gln Gln Ala Leu Gln Gln Glu
            260                 265                 270

Phe Glu Lys Gln Ile Ser Asp Ser Ser Lys Ser Glu Lys
            275                 280                 285

<210> SEQ ID NO 3
<211> LENGTH: 268
<212> TYPE: PRT
<213> ORGANISM: Helicobacter pylori

<400> SEQUENCE: 3

Met Ser Glu Lys Glu Arg Leu Asn Glu Val Ile Leu Glu Glu Glu Asn
1               5                  10                  15

Asn Gly Ser Gly Thr Lys Lys Val Phe Leu Ile Val Ala Ile Ala Ile
            20                  25                  30

Ile Ile Leu Ala Val Leu Leu Met Val Phe Trp Lys Ser Thr Arg Val
        35                  40                  45

Ala Pro Lys Glu Thr Phe Leu Gln Thr Asp Ser Gly Met Gln Lys Ile
    50                  55                  60

Gly Asn Thr Lys Asp Glu Lys Asp Asp Glu Phe Glu Ser Leu Asn
65                  70                  75                  80

Met Asp Ser Pro Lys Gln Glu Asp Lys Leu Asp Lys Val Val Asp Asn
                85                  90                  95

Ile Lys Lys Gln Glu Ser Glu Asn Ser Met Pro Ile Gln Thr Asp Gln
            100                 105                 110

Ala Gln Met Glu Met Lys Thr Thr Glu Glu Lys Gln Glu Ser Gln Lys
```

```
             115                 120                 125
Glu Leu Lys Ala Val Glu Pro Ile Pro Met Ser Thr Gln Lys Glu Ser
        130                 135                 140

Gln Ala Val Ala Lys Lys Glu Thr Pro His Lys Lys Pro Lys Val Ala
145                 150                 155                 160

Pro Lys Asp Lys Glu Ala His Lys Asp Lys Ala Lys His Ala Ala Lys
                165                 170                 175

Glu Pro Lys Val Lys Lys Glu Ala Arg Lys Glu Val Ser Lys Lys Ala
            180                 185                 190

Asn Ser Lys Thr Asn Leu Thr Lys Gly His Tyr Leu Gln Val Gly Val
        195                 200                 205

Phe Ala His Thr Pro Asn Lys Ala Phe Leu Gln Glu Phe Asn Gln Phe
210                 215                 220

Pro His Lys Ile Glu Asp Arg Gly Ala Thr Lys Arg Tyr Leu Ile Gly
225                 230                 235                 240

Pro Tyr Lys Ser Lys Gln Glu Ala Leu Met His Ala Asp Glu Val Ser
                245                 250                 255

Lys Lys Met Thr Lys Pro Val Val Ile Glu Val Arg
            260                 265
```

<210> SEQ ID NO 4
<211> LENGTH: 329
<212> TYPE: PRT
<213> ORGANISM: Helicobacter pylori

<400> SEQUENCE: 4

```
Met Ser Asn Ser Met Leu Asp Lys Asn Lys Ala Ile Leu Thr Gly Gly
1               5                   10                  15

Gly Ala Leu Leu Leu Gly Leu Ile Val Leu Phe Tyr Leu Ala Tyr Arg
            20                  25                  30

Pro Lys Ala Glu Val Leu Gln Gly Phe Leu Glu Ala Arg Glu Tyr Ser
        35                  40                  45

Val Ser Ser Lys Val Pro Gly Arg Ile Glu Lys Val Phe Val Lys Lys
50                  55                  60

Gly Asp Arg Ile Lys Lys Gly Asp Leu Val Phe Ser Ile Ser Ser Pro
65                  70                  75                  80

Glu Leu Glu Ala Lys Leu Ala Gln Ala Glu Ala Gly His Lys Ala Ala
                85                  90                  95

Lys Ala Val Ser Asp Glu Val Lys Arg Gly Ser Arg Asp Glu Thr Ile
            100                 105                 110

Asn Ser Ala Arg Asp Val Trp Gln Ala Ala Lys Ser Gln Ala Asn Leu
        115                 120                 125

Ala Lys Glu Thr Tyr Lys Arg Val Gln Asp Leu Tyr Asp Asn Gly Val
130                 135                 140

Ala Ser Leu Gln Lys Arg Asp Glu Ala Tyr Ala Ala Tyr Glu Ser Thr
145                 150                 155                 160

Lys Tyr Asn Glu Ser Ala Ala Tyr Gln Lys Tyr Lys Met Ala Leu Gly
                165                 170                 175

Gly Ala Ser Ser Glu Ser Lys Ile Ala Ala Lys Ala Lys Glu Ser Ala
            180                 185                 190

Ala Leu Gly Gln Val Asn Glu Val Glu Ser Tyr Leu Lys Asp Val Lys
        195                 200                 205

Ala Leu Ala Pro Ile Asp Gly Glu Val Ser Asn Val Leu Leu Ser Gly
210                 215                 220
```

```
Gly Glu Leu Ser Pro Lys Gly Phe Pro Val Val Leu Met Ile Asp Leu
225                 230                 235                 240

Lys Asp Ser Trp Leu Lys Ile Ser Val Pro Glu Lys Tyr Leu Asn Glu
            245                 250                 255

Phe Lys Val Gly Lys Glu Phe Glu Gly Tyr Ile Pro Ala Leu Lys Arg
        260                 265                 270

Ser Ala Lys Phe Arg Val Lys Tyr Leu Ser Val Met Gly Asp Phe Ala
    275                 280                 285

Thr Trp Lys Ala Thr Asn Ser Asn Thr Tyr Asp Met Lys Ser Tyr
290                 295                 300

Glu Val Glu Ala Ile Pro Leu Glu Glu Leu Glu Asn Phe Arg Val Gly
305                 310                 315                 320

Met Ser Val Leu Val Thr Ile Lys Pro
                325

<210> SEQ ID NO 5
<211> LENGTH: 477
<212> TYPE: PRT
<213> ORGANISM: Helicobacter pylori

<400> SEQUENCE: 5

Met Asn Thr Ile Ile Arg Tyr Ala Ser Leu Trp Gly Leu Cys Ile Thr
1               5                   10                  15

Leu Thr Leu Ala Gln Thr Pro Ser Lys Thr Pro Asp Glu Ile Lys Gln
            20                  25                  30

Ile Leu Asn Asn Tyr Ser His Lys Asn Leu Lys Leu Ile Asp Pro Pro
        35                  40                  45

Thr Ser Ser Leu Glu Ala Thr Pro Gly Phe Leu Pro Ser Pro Lys Glu
    50                  55                  60

Thr Ala Thr Thr Ile Asn Gln Glu Ile Ala Lys Tyr His Glu Lys Ser
65                  70                  75                  80

Asp Lys Ala Ala Leu Gly Leu Tyr Glu Leu Leu Lys Gly Ala Thr Thr
                85                  90                  95

Asn Leu Ser Leu Gln Ala Gln Glu Leu Ser Val Lys Gln Ala Met Lys
            100                 105                 110

Asn His Thr Ile Ala Lys Ala Met Phe Leu Pro Thr Leu Asn Ala Ser
        115                 120                 125

Tyr Asn Phe Lys Asn Glu Ala Arg Asp Thr Pro Glu Tyr Lys His Tyr
    130                 135                 140

Asn Thr Gln Gln Leu Gln Ala Gln Val Thr Leu Asn Val Phe Asn Gly
145                 150                 155                 160

Phe Ser Asn Val Asn Asn Val Lys Glu Lys Ser Ala Thr Tyr Arg Ser
                165                 170                 175

Thr Val Ala Asn Leu Glu Tyr Ser Arg Gln Ser Val Tyr Leu Gln Val
            180                 185                 190

Val Gln Gln Tyr Tyr Glu Tyr Phe Asn Asn Leu Ala Arg Met Ile Ala
        195                 200                 205

Leu Gln Lys Lys Leu Glu Gln Ile Gln Thr Asp Ile Lys Arg Val Thr
    210                 215                 220

Lys Leu Tyr Asp Lys Gly Leu Thr Thr Ile Asp Asp Leu Gln Ser Leu
225                 230                 235                 240

Lys Ala Gln Gly Asn Leu Ser Glu Tyr Asp Ile Leu Asp Met Gln Phe
                245                 250                 255

Ala Leu Glu Gln Asn Arg Leu Thr Leu Glu Tyr Leu Thr Asn Leu Ser
            260                 265                 270
```

```
Val Lys Asn Leu Lys Lys Thr Thr Ile Asp Ala Pro Asn Leu Gln Leu
        275                 280                 285

Arg Glu Arg Gln Asp Leu Val Ser Leu Arg Glu Gln Ile Ser Ala Leu
    290                 295                 300

Arg Tyr Gln Asn Lys Gln Leu Asn Tyr Tyr Pro Lys Ile Asp Val Phe
305                 310                 315                 320

Asp Ser Trp Leu Phe Trp Ile Gln Lys Pro Ala Tyr Ala Thr Gly Arg
                325                 330                 335

Phe Gly Asn Phe Tyr Pro Gly Gln Gln Asn Thr Ala Gly Val Thr Ala
                340                 345                 350

Thr Leu Asn Ile Phe Asp Asp Ile Gly Leu Ser Leu Gln Lys Gln Ser
                355                 360                 365

Ile Met Leu Gly Gln Leu Ala Asn Glu Lys Asn Leu Ala Tyr Lys Lys
        370                 375                 380

Leu Glu Gln Glu Lys Asp Glu Gln Leu Tyr Arg Lys Ser Leu Asp Ile
385                 390                 395                 400

Ala Arg Ala Lys Ile Glu Ser Ser Lys Ala Ser Leu Asp Ala Ala Asn
                405                 410                 415

Leu Ser Phe Ala Asn Ile Lys Arg Lys Tyr Asp Ala Asn Leu Val Asp
                420                 425                 430

Phe Thr Thr Tyr Leu Arg Gly Leu Thr Thr Arg Phe Asp Ala Glu Val
                435                 440                 445

Ala Tyr Asn Leu Ala Leu Asn Asn Tyr Glu Val Gln Lys Ala Asn Tyr
        450                 455                 460

Ile Phe Asn Ser Gly His Lys Ile Asp Asp Tyr Val His
465                 470                 475

<210> SEQ ID NO 6
<211> LENGTH: 501
<212> TYPE: PRT
<213> ORGANISM: Helicobacter pylori

<400> SEQUENCE: 6

Met Lys Met Ile Leu Phe Asn Gln Asn Pro Met Ile Glu Lys Leu Leu
1               5                   10                  15

Glu Ser Val Ser Lys Lys Leu Glu Leu Ser Ile Glu Asn Phe Asn His
            20                  25                  30

Tyr Gln Glu Leu Ser Ala Arg Leu Lys Gly Asp Pro Glu Trp Leu Leu
        35                  40                  45

Ile Ala Asp Asp Glu Cys Leu Glu Lys Leu Asp Gln Val Asp Trp Leu
    50                  55                  60

Glu Leu Lys Glu Thr Ile Ser Gln Asn Lys Asn Ser Val Cys Met Tyr
65                  70                  75                  80

Lys Lys Gly Asn Glu Ala Gln Pro Phe Leu Glu Gly Phe Glu Met Lys
                85                  90                  95

Ile Lys Lys Pro Phe Leu Pro Thr Glu Met Leu Lys Val Leu Gln Lys
            100                 105                 110

Lys Leu Gly Ser Asn Ala Ser Glu Leu Glu Pro Ser Gln Asn Leu Asp
        115                 120                 125

Pro Thr Gln Glu Ile Leu Glu Thr Asn Trp Asp Leu Glu Asn Leu
    130                 135                 140

Gly Asp Leu Glu Ala Leu Ala Lys Glu Pro Asn Asn Glu Glu Gln
145                 150                 155                 160

Leu Leu Pro Thr Leu Asn Glu Gln Glu Gly Glu Thr Pro Lys Glu Glu
```

```
              165                 170                 175
Ala Gln Glu Glu Val Lys Lys Glu Val Lys Glu Met Gln Glu Glu
                180                 185                 190

Val Lys Glu Lys Gln Lys Gln Glu Val Ala Glu Asn Pro Gln Asp Glu
                195                 200                 205

Glu Lys Pro Lys Asp Asp Glu Thr Gln Gly Ser Val Glu Pro Pro Lys
            210                 215                 220

Asp Glu Glu Val Ser Lys Glu Leu Glu Thr Gln Glu Glu Leu Glu Thr
225                 230                 235                 240

Pro Lys Glu Glu Thr Gln Glu Gln Glu Pro Ile Lys Glu Glu Thr Gln
                245                 250                 255

Glu Ile Lys Glu Glu Lys Gln Glu Lys Thr Gln Asp Ser Pro Ser Ala
                260                 265                 270

Gln Glu Leu Glu Ala Met Gln Glu Leu Val Lys Glu Ile Gln Glu Asn
                275                 280                 285

Ser Asn Asp Gln Glu Asn Lys Lys Glu Thr Gln Glu Thr Gln Glu Asn
            290                 295                 300

Thr Glu Thr Pro Gln Asp Ile Glu Thr Gln Glu Leu Glu Ile Pro Lys
305                 310                 315                 320

Glu Glu Glu Thr Gln Glu Val Ala Glu Lys Thr Gln Val Gln Gly Leu
                325                 330                 335

Glu Lys Glu Glu Ile Ala Glu Thr Pro Gln Lys Glu Ile Gln Glu
                340                 345                 350

Thr Gln Asp Glu Thr Pro Gln Glu Leu Glu Ala Gln Asp Gly Lys Leu
                355                 360                 365

Gln Glu Asn Glu Thr Pro Lys Asp Glu Ser Met Gln Glu Ser Ala Gln
            370                 375                 380

Asn Leu Gln Asp Lys Glu Thr Pro Gln Glu Thr Gln Glu Asp His
385                 390                 395                 400

Tyr Glu Ser Ile Glu Asp Ile Pro Glu Pro Val Met Ala Lys Ala Met
                405                 410                 415

Gly Glu Glu Leu Pro Phe Leu Asn Glu Ala Val Ala Lys Ile Pro Asn
                420                 425                 430

Asn Glu Asn Asp Thr Glu Thr Pro Lys Glu Ser Asp Ile Lys Ala Pro
            435                 440                 445

Gln Glu Lys Glu Ser Asp Lys Thr Ser Ser Pro Leu Glu Leu Arg
                450                 455                 460

Leu Asn Leu Gln Asp Leu Leu Lys Ser Leu Asn Gln Glu Ser Leu Lys
465                 470                 475                 480

Ser Leu Leu Glu Asn Lys Thr Leu Ser Ile Lys Ile Thr Leu Glu Asp
                485                 490                 495

Lys Lys Pro Asn Glu
            500

<210> SEQ ID NO 7
<211> LENGTH: 195
<212> TYPE: PRT
<213> ORGANISM: Helicobacter pylori

<400> SEQUENCE: 7

Met Gly Tyr Ile Pro Tyr Val Ile Glu Asn Thr Glu Arg Gly Glu Arg
1               5                   10                  15

Ser Tyr Asp Ile Tyr Ser Arg Leu Leu Lys Asp Arg Ile Val Leu Leu
            20                  25                  30
```

```
Ser Gly Glu Ile Asn Asp Ser Val Ala Ser Ser Ile Val Ala Gln Leu
         35                  40                  45

Leu Phe Leu Glu Ala Glu Asp Pro Glu Lys Asp Ile Gly Leu Tyr Ile
 50                  55                  60

Asn Ser Pro Gly Gly Val Ile Thr Ser Gly Leu Ser Ile Tyr Asp Thr
 65                  70                  75                  80

Met Asn Phe Ile Arg Pro Asp Val Ser Thr Ile Cys Ile Gly Gln Ala
                 85                  90                  95

Ala Ser Met Gly Ala Phe Leu Leu Ser Cys Gly Ala Lys Gly Lys Arg
             100                 105                 110

Phe Ser Leu Pro His Ser Arg Ile Met Ile His Gln Pro Leu Gly Gly
         115                 120                 125

Ala Gln Gly Gln Ala Ser Asp Ile Glu Ile Ile Ser Asn Glu Ile Leu
130                 135                 140

Arg Leu Lys Gly Leu Met Asn Ser Ile Leu Ala Gln Asn Ser Gly Gln
145                 150                 155                 160

Ser Leu Glu Gln Ile Ala Lys Asp Thr Asp Arg Asp Phe Tyr Met Ser
                165                 170                 175

Ala Lys Glu Ala Lys Glu Tyr Gly Leu Ile Asp Lys Val Leu Gln Lys
            180                 185                 190

Asn Val Lys
        195

<210> SEQ ID NO 8
<211> LENGTH: 606
<212> TYPE: DNA
<213> ORGANISM: Helicobacter pylori

<400> SEQUENCE: 8
atgcgtttgc acactgcctt ttttggtatt aattcgttgc ttgtcgccac tcttttgata      60
agcggttgca gtctctttaa aaagcgtaac actaacgctc agctaatccc cccttcagct     120
aacgggttgc aagcccccat ttatccccca accaatttca ccccagaaa gagcattcag      180 cctctcccaa gccctcgcct tgagaataac gatcagccca tcattagctc taatcccact     240
aacgctatcc ctaacacccc cattctcacg cccaataatg tcattgagtt gaatgcggtg     300
ggcatgggtg tggctccaga atccaccatt tcgccctctc aagctctagc tttagctaag     360
cgagcggcta ttgttgatgg ctaccgccag ttgggtgaaa aatgtatgg catcagagtg      420 aacgctcaag acaccgtcaa agacatggtt ttacaaaatt ccgtgattaa acgagagtg      480 aatgccctca ttcgtaacgc tgaaatcact gagactatct ataaagacgg cttgtgccag     540
gtaagcatgg agcttaaatt agacggcagg atttggtatc gtattttgag cggatcgaga     600
ggataa                                                                 606

<210> SEQ ID NO 9
<211> LENGTH: 858
<212> TYPE: DNA
<213> ORGANISM: Helicobacter pylori

<400> SEQUENCE: 9
gtgaagcgaa ttttattttt tttagcggct acgacttttt tgttgagagc agaaacggct      60
tctgctacta ttaacactac agttgatccc aatgttatgt ttctgaaag ctccacaggg      120 aatgtgaaaa agaccgcaa gagggtttta agagcatgg ttgatttaga aaaagagcgc       180
gtgaagaatt taaccagta ttctgaaacc aagatgagta agggcgattt atccgctttt      240
```

-continued

| | |
|---|---|
| ggagctttct ttaaggggag tttggaagat tgcgtggagc aaaagatttg ttactatgag | 300 |
| cataggaatg gcaaggtttc tttttgtggtg aatgacagag aaaagttttta taagcatgtg | 360 |
| cttaaagact tagggacaga gctttcactc cccttgttca actggcttta caaaggctca | 420 |
| gattttgggg ctttgcatga gcagtttggg gacatgtatg atgggtatat caaatacttg | 480 |
| atcagcatgg ttagggtgag ccaaaaagaa aaggctagaa aagtggatgc aatcgttctt | 540 |
| aaaaaaatgg aagaacaagc tgagaaagac actaaggcag cattccaaaa gaggagcagt | 600 |
| ggggagcttg aaagccatac tgatagccct gaatttataa gctcttctaa gacacagaat | 660 |
| tcttctaacc cagatctaga ccctatgact aacgctaaca cgctcaaaga aacagcttca | 720 |
| aaagagccag agacttcttc aaaaaaggaa aaaaagccca agaaaaaacg acgcctttca | 780 |
| aagaaagaaa agcaacaaca ggccttacaa caagagtttg aaaagcaaat tagcgactct | 840 |
| agtaagtctg aaaaatag | 858 |

<210> SEQ ID NO 10
<211> LENGTH: 807
<212> TYPE: DNA
<213> ORGANISM: Helicobacter pylori

<400> SEQUENCE: 10

| | |
|---|---|
| atgtcagaaa aagaaagact gaatgaagtg atcttagaag aagagaataa tgggagtggt | 60 |
| actaaaaagg tgttttttgat cgtggccata gccattatca ttttggcggt gcttttaatg | 120 |
| gtgtttttgga aaagcaccag agtcgctcct aaagagactt ttttacaaac cgatagtggc | 180 |
| atgcaaaaaa taggcaacac taagatgag aaaaaagacg atgagtttga aagcttgaat | 240 |
| atggattctc ccaaacaaga agacaagtta gacaaagtgg tggataatat taaaaaacaa | 300 |
| gagagtgaaa attctatgcc cattcaaacc gatcaagctc aaatggagat gaaaacaaca | 360 |
| gaagaaaaac aagaatctca aaaagaatta aaagctgttg agcctattcc catgagcact | 420 |
| caaaaagaat ctcaggctgt ggctaaaaaa gaaacccccc ataaaaagcc taagtagcg | 480 |
| ccaaaagata agaagcgca taagataaa gctaagcatg cagctaaaga gccaaaagtc | 540 |
| aaaaaagaag ctcgtaaaga agtttctaag aaagctaatt ctaaaaccaa tcttactaaa | 600 |
| gggcattatt tgcaagtggg ggttttttgcg cacacgccca acaaagcctt tttacaagag | 660 |
| tttaatcaat tcccccataa aattgaagat aggggggcta ctaaacgcta cctcataggc | 720 |
| ccttataaga gcaagcaaga agccttaatg catgccgatg aagtcagcaa gaagatgact | 780 |
| aaaccggttg tcatagaagt gcggtag | 807 |

<210> SEQ ID NO 11
<211> LENGTH: 990
<212> TYPE: DNA
<213> ORGANISM: Helicobacter pylori

<400> SEQUENCE: 11

| | |
|---|---|
| atgtcaaata gcatgttgga taaaaataaa gcgattctta caggggggtgg ggctttattg | 60 |
| ttagggctaa tcgtgctttt ttatttggct tatcgcccta aggctgaagt gttgcaaggg | 120 |
| tttttagagg ctagggaata cagcgtgagc tctaaagtcc ctggccgcat tgaaaaggtg | 180 |
| tttgttaaaa aaggcgatcg cattaaaaag ggcgatttag tttttagcat ttctagccct | 240 |
| gaattagaag ccaagctcgc tcaagctgaa gccgggcata aagccgctaa agccgttagc | 300 |
| gatgaagtga aaagaggctc aagagatgaa acgatcaatt ctgcgaggga cgtttggcaa | 360 |
| gcggcaaaat cccaagcgaa tttggctaaa gagacttata agcgcgttca agatttgtat | 420 |

-continued

```
gacaatggcg tggcgagttt gcaaaagcgc gatgaagcct atgcggctta tgaaagcacc    480
aaatacaacg agagcgcggc ttaccaaaag tataaaatgg ctttaggggg ggcgagttct    540
gaaagcaaga ttgccgctaa ggctaaagag agcgcggctt tagggcaagt gaatgaagtg    600
gaatcctact taaaagacgt caaagcccta gcccctattg atggggaagt gagtaacgtg    660
cttttaagcg gtggcgagct tagccctaag ggctttcctg tggtgctcat gatagattta    720
aaggatagtt ggttaaaaat cagcgtgcct gaaaagtatt tgaacgagtt taaagtgggt    780
aaggaatttg aaggctatat cccagcgttg aaaagaagcg cgaaattcag ggtcaaatat    840
ttgagcgtga tgggggattt tgcgacctgg aaagcgacga ataattccaa cacttacgac    900
atgaaaagct atgaagtgga ggccataccc ttagaagagt tggaaaactt tagggtgggg    960
atgagcgtgt tggttaccat taaaccttaa                                     990
```

<210> SEQ ID NO 12
<211> LENGTH: 1434
<212> TYPE: DNA
<213> ORGANISM: Helicobacter pylori

<400> SEQUENCE: 12

```
atgaatacta ttataagata tgcgagttta tggggcttgt gtattactct aactctagcg     60
caaacccccct ctaaaacccc tgatgaaatc aagcaaatcc ttaacaatta tagccataag   120
aatttaaagc tcattgatcc gccgacaagt tctttagaag cgacaccggg ttttttaccc    180
tcgcctaaag aaacagcgac cacgatcaat caagagatcg ctaaatacca tgaaaaaagc    240
gataaagccg ctttggggct ttatgaattg ctaaaggggg ctaccaccaa tctcagtttg    300
caagcgcaag aactcagtgt caagcaagcg atgaagaacc acaccatcgc caaagcgatg    360
tttttgccta ctttgaacgc gagttataat tttaaaaatg aagctaggga tactccagaa    420
tataagcatt ataacaccca acaactccaa gctcaagtca cattgaatgt gtttaatggc    480
tttagcaatg tgaataatgt caaagaaaag tctgcgactt accgatccac tgtggctaat    540
ttagaatata gccgccaaag cgtgtatttg caagtggtgc aacaatacta cgagtatttt    600
aacaatctcg ctcgcatgat cgctttgcaa aagaaattag agcaaatcca aacggacatt    660
aaaagggtta ctaagctcta tgacaaaggg ctgaccacga ttgatgattt acaaagctta    720
aaagcgcaag ggaatttgag cgaatacgat attttggaca tgcaatttgc tttggagcaa    780
aaccgcttga ctttagaata cctcactaac ctcagtgtga aaaatttgaa aaagaccacg    840
attgatgcgc ctaatttgca attaagagaa aggcaggatt tggtttcttt aagggagcag    900
atttctgcac tcagatacca aaacaagcaa ctcaattatt accccaagat agatgtgttt    960
gactcatggc ttttttggat ccaaaaaccc gcttatgcca cagggcgttt tgggaatttc   1020
tacccaggtc agcaaaatac ggctggggtt actgcgactt tgaatatttt tgatgatata   1080
gggttgagct tgcaaaaaca atccatcatg ctaggccaat tagcgaatga aaagaattta   1140
gcgtataaaa aattggagca agaaaaagac gaacagcttt acagaaagtc gcttgatatt   1200
gccagagcta agattgaatc ttcaaaggct agtttggatg cggccaatct ttcttttgcc   1260
aatattaaaa ggaaatacga cgctaattta gtggatttca ctacctattt aaggggctta   1320
accacgcgct ttgatgcaga agtggcttac aatttagcgc tcaacaatta cgaagtgcaa   1380
aaagccaatt acatttttaa cagcgggcat aaaatagacg actatgtgca ttaa          1434
```

<210> SEQ ID NO 13

```
<211> LENGTH: 1506
<212> TYPE: DNA
<213> ORGANISM: Helicobacter pylori

<400> SEQUENCE: 13
atgaaaatga ttctattcaa ccaaaacccc atgattgaaa agctgcttga gagtgtttct    60
aagaaattag aattatccat agaaaatttt aaccactatc aagagttatc cgcgcgcctt   120
aaaggagatc cagaatggct tttgatagcc gatgatgaat gtttggaaaa actagatcaa   180
gtggattggc tagagttaaa agaaaccatc tctcaaaata aaaacagcgt gtgcatgtat   240
aaaaagggca atgaagcgca gcccttttta gagggctttg agatgaaaat caaaaagcct   300 ttttttaccca ctgaaatgtt gaaagtcctt caaaaaaagc ttggctctaa cgcaagcgag   360
ctagagccta gccagaattt agacccaact caagaaattt tagaaaccaa ttgggatgag   420
ttggaaaatc taggcgattt agaagcccta gccaagaag agcctaacaa cgaagagcaa   480
ttgctcccca cttttaaacga gcaagaagga gaaactccta agaagaagc gcaagaagag   540 gttaaaaaag aagaagttaa agaaatgcaa gaagaagtta agaaaaaca aaaacaagaa   600 gttgcagaaa accccccaaga tgaagaaaag cccaaagatg atgaaacgca agggagcgtt   660 gaaccccca aagatgaaga agtttctaaa gaattgaaaa cgcaagaaga attagaaacc   720
cctaaagaag aaacgcaaga acaagagcca atcaaagaag aaacgcaaga aattaaggag   780
gaaaaacaag agaaaacaca agattcccca agcgcgcaag aattagaagc catgcaagaa   840
ttagtcaaag aaatccaaga aaattctaac gaccaagaga taaaaagga acccaagaa   900 acccaagaaa acacagaaac accgcaagat atagaaacgc aggaattaga aattcctaaa   960
gaagaagaaa cacaagaagt cgcagaaaaa acacaggtgc aaggattaga aaagaagaa  1020 attgcagaaa cgccccaaga aaagaaatc caagaaaccc aagatgaaac gccccaagaa  1080
ttagaagccc aagatgaaaa actccaagaa aacgaaaccc ccaaagatga agcatgcaa  1140 gaaagtgcac aaaatttaca agataaagaa accccccaag aagaaaccca agaagatcat  1200
tacgaaagca ttgaagacat tcctgagccg gtgatggcta agcgatggg ggaagaattg  1260 cccttttga tgaagctgt tgcaaaaatt cctaataatg agaacgacac agaaacccct  1320
aaagagagcg atataaaagc cccacaagaa aaagaagaaa gcgataaaac ttccagcccc  1380
ctagaattgc gcttgaattt gcaggattta ttaaaaagcc tcaatcaaga gtccttaaaa  1440
agccttttag aaaacaaaac cttaagcatt aaaatcactt tagaggataa aaaacctaat  1500
gaataa                                                               1506

<210> SEQ ID NO 14
<211> LENGTH: 588
<212> TYPE: DNA
<213> ORGANISM: Helicobacter pylori

<400> SEQUENCE: 14
atgggataca ttccttatgt aatagaaaat acagagcgtg gcgaacgcag ttatgatatt    60
tactcacgcc ttttaaagga tcgcatcgtt ttattgagcg gtgagattaa cgatagcgtg   120
gcgtcttcta tcgtggccca actcttgttt ttggaagccg aagatcctga aaagacatt   180 ggcttgtata tcaattctcc cggtggggtg ataacgagcg gtcttagcat ttatgacacc   240
atgaatttta tccgccctga tgtttccacg atttgcatcg gtcaagcggc ttctatgggg   300 gcgttttac taagctgtgg ggctaagggc aagcgctttt cactgcccca ttcaaggatt   360
atgatccacc agcctttagg ggggctcaa gggcaagcga gcgatattga aatcatttct   420
```

```
aacgagatcc ttaggcttaa gggtttgatg aattctattt tggctcaaaa ctcagggcag    480
agtttggagc aaatcgctaa agacacggat agggattttt acatgagcgc taaagaagct    540
aaagagtatg gcttgattga taaagtgtta cagaaaaacg tgaagtga                 588
```

```
<210> SEQ ID NO 15
<211> LENGTH: 175
<212> TYPE: PRT
<213> ORGANISM: Artificial Sequence
<220> FEATURE:
<223> OTHER INFORMATION: aa 34-201 of jhp_0775 + C-terminal His-tag

<400> SEQUENCE: 15
```

```
Met Gln Leu Ile Pro Pro Ser Ala Asn Gly Leu Gln Ala Pro Ile Tyr
1               5                   10                  15

Pro Pro Thr Asn Phe Thr Pro Arg Lys Ser Ile Gln Pro Leu Pro Ser
            20                  25                  30

Pro Arg Leu Glu Asn Asn Asp Gln Pro Ile Ile Ser Ser Asn Pro Thr
        35                  40                  45

Asn Ala Ile Pro Asn Thr Pro Ile Leu Thr Pro Asn Asn Val Ile Glu
    50                  55                  60

Leu Asn Ala Val Gly Met Gly Val Ala Pro Glu Ser Thr Ile Ser Pro
65                  70                  75                  80

Ser Gln Ala Leu Ala Leu Ala Lys Arg Ala Ala Ile Val Asp Gly Tyr
                85                  90                  95

Arg Gln Leu Gly Glu Lys Met Tyr Gly Ile Arg Val Asn Ala Gln Asp
            100                 105                 110

Thr Val Lys Asp Met Val Leu Gln Asn Ser Val Ile Lys Thr Arg Val
        115                 120                 125

Asn Ala Leu Ile Arg Asn Ala Glu Ile Thr Glu Thr Ile Tyr Lys Asp
    130                 135                 140

Gly Leu Cys Gln Val Ser Met Glu Leu Lys Leu Asp Gly Arg Ile Trp
145                 150                 155                 160

Tyr Arg Ile Leu Ser Gly Ser Arg Gly His His His His His His
                165                 170                 175
```

```
<210> SEQ ID NO 16
<211> LENGTH: 270
<212> TYPE: PRT
<213> ORGANISM: Artificial Sequence
<220> FEATURE:
<223> OTHER INFORMATION: aa 23-285 of jhp_0119 + C-terminal His-tag

<400> SEQUENCE: 16
```

```
Met Thr Ile Asn Thr Thr Val Asp Pro Asn Val Met Phe Ser Glu Ser
1               5                   10                  15

Ser Thr Gly Asn Val Lys Lys Asp Arg Lys Arg Val Leu Lys Ser Met
            20                  25                  30

Val Asp Leu Glu Lys Glu Arg Val Lys Asn Phe Asn Gln Tyr Ser Glu
        35                  40                  45

Thr Lys Met Ser Lys Gly Asp Leu Ser Ala Phe Gly Ala Phe Phe Lys
    50                  55                  60

Gly Ser Leu Glu Asp Cys Val Glu Gln Lys Ile Cys Tyr Tyr Glu His
65                  70                  75                  80

Arg Asn Gly Lys Val Ser Phe Val Val Asn Asp Arg Glu Lys Phe Tyr
                85                  90                  95

Lys His Val Leu Lys Asp Leu Gly Thr Glu Leu Ser Leu Pro Leu Phe
```

```
                100             105                 110
Asn Trp Leu Tyr Lys Gly Ser Asp Phe Gly Ala Leu His Glu Gln Phe
            115                 120                 125
Gly Asp Met Tyr Asp Gly Tyr Ile Lys Tyr Leu Ile Ser Met Val Arg
        130                 135                 140
Val Ser Gln Lys Glu Lys Ala Arg Lys Val Asp Ala Ile Val Leu Lys
145                 150                 155                 160
Lys Met Glu Glu Gln Ala Glu Lys Asp Thr Lys Ala Ala Phe Gln Lys
                165                 170                 175
Arg Ser Ser Gly Glu Leu Glu Ser His Thr Asp Ser Pro Glu Phe Ile
            180                 185                 190
Ser Ser Ser Lys Thr Gln Asn Ser Ser Asn Pro Asp Leu Asp Pro Met
        195                 200                 205
Thr Asn Ala Asn Thr Leu Lys Glu Thr Ala Ser Lys Glu Pro Glu Thr
210                 215                 220
Ser Ser Lys Lys Glu Lys Pro Lys Lys Arg Arg Leu Ser Lys
225                 230                 235                 240
Lys Glu Lys Gln Gln Gln Ala Leu Gln Gln Glu Phe Glu Lys Gln Ile
                245                 250                 255
Ser Asp Ser Ser Lys Ser Glu Lys His His His His His
            260                 265                 270

<210> SEQ ID NO 17
<211> LENGTH: 232
<212> TYPE: PRT
<213> ORGANISM: Artificial Sequence
<220> FEATURE:
<223> OTHER INFORMATION: aa 44-268 of jhp_0173 + C-terminal His-tag

<400> SEQUENCE: 17

Met Lys Ser Thr Arg Val Ala Pro Lys Glu Thr Phe Leu Gln Thr Asp
1               5                   10                  15
Ser Gly Met Gln Lys Ile Gly Asn Thr Lys Asp Glu Lys Lys Asp
            20                  25                  30
Glu Phe Glu Ser Leu Asn Met Asp Ser Pro Lys Gln Glu Asp Lys Leu
        35                  40                  45
Asp Lys Val Val Asp Asn Ile Lys Lys Gln Glu Ser Glu Asn Ser Met
50                  55                  60
Pro Ile Gln Thr Asp Gln Ala Gln Met Glu Met Lys Thr Thr Glu Glu
65                  70                  75                  80
Lys Gln Glu Ser Gln Lys Glu Leu Lys Ala Val Glu Pro Ile Pro Met
                85                  90                  95
Ser Thr Gln Lys Glu Ser Gln Ala Val Ala Lys Lys Glu Thr Pro His
            100                 105                 110
Lys Lys Pro Lys Val Ala Pro Lys Asp Lys Glu Ala His Lys Asp Lys
        115                 120                 125
Ala Lys His Ala Ala Lys Glu Pro Lys Val Lys Glu Ala Arg Lys
130                 135                 140
Glu Val Ser Lys Lys Ala Asn Ser Lys Thr Asn Leu Thr Lys Gly His
145                 150                 155                 160
Tyr Leu Gln Val Gly Val Phe Ala His Thr Pro Asn Lys Ala Phe Leu
                165                 170                 175
Gln Glu Phe Asn Gln Phe Pro His Lys Ile Glu Asp Arg Gly Ala Thr
            180                 185                 190
Lys Arg Tyr Leu Ile Gly Pro Tyr Lys Ser Lys Gln Glu Ala Leu Met
```

```
                195                 200                 205
His Ala Asp Glu Val Ser Lys Lys Met Thr Lys Pro Val Val Ile Glu
    210                 215                 220

Val Arg His His His His His His
225                 230

<210> SEQ ID NO 18
<211> LENGTH: 305
<212> TYPE: PRT
<213> ORGANISM: Artificial Sequence
<220> FEATURE:
<223> OTHER INFORMATION: aa 32-329 of jhp_1381 + C-terminal His-tag

<400> SEQUENCE: 18

Met Arg Pro Lys Ala Glu Val Leu Gln Gly Phe Leu Glu Ala Arg Glu
1               5                   10                  15

Tyr Ser Val Ser Ser Lys Val Pro Gly Arg Ile Glu Lys Val Phe Val
                20                  25                  30

Lys Lys Gly Asp Arg Ile Lys Lys Gly Asp Leu Val Phe Ser Ile Ser
            35                  40                  45

Ser Pro Glu Leu Glu Ala Lys Leu Ala Gln Ala Glu Ala Gly His Lys
50                  55                  60

Ala Ala Lys Ala Val Ser Asp Glu Val Lys Arg Gly Ser Arg Asp Glu
65                  70                  75                  80

Thr Ile Asn Ser Ala Arg Asp Val Trp Gln Ala Lys Ser Gln Ala
                85                  90                  95

Asn Leu Ala Lys Glu Thr Tyr Lys Arg Val Gln Asp Leu Tyr Asp Asn
                100                 105                 110

Gly Val Ala Ser Leu Gln Lys Arg Asp Glu Ala Tyr Ala Ala Tyr Glu
            115                 120                 125

Ser Thr Lys Tyr Asn Glu Ser Ala Ala Tyr Gln Lys Tyr Lys Met Ala
130                 135                 140

Leu Gly Gly Ala Ser Ser Glu Ser Lys Ile Ala Ala Lys Ala Lys Glu
145                 150                 155                 160

Ser Ala Ala Leu Gly Gln Val Asn Glu Val Glu Ser Tyr Leu Lys Asp
                165                 170                 175

Val Lys Ala Leu Ala Pro Ile Asp Gly Glu Val Ser Asn Val Leu Leu
            180                 185                 190

Ser Gly Gly Glu Leu Ser Pro Lys Gly Phe Pro Val Val Leu Met Ile
        195                 200                 205

Asp Leu Lys Asp Ser Trp Leu Lys Ile Ser Val Pro Glu Lys Tyr Leu
210                 215                 220

Asn Glu Phe Lys Val Gly Lys Glu Phe Glu Gly Tyr Ile Pro Ala Leu
225                 230                 235                 240

Lys Arg Ser Ala Lys Phe Arg Val Lys Tyr Leu Ser Val Met Gly Asp
                245                 250                 255

Phe Ala Thr Trp Lys Ala Thr Asn Asn Ser Asn Thr Tyr Asp Met Lys
            260                 265                 270

Ser Tyr Glu Val Glu Ala Ile Pro Leu Glu Glu Leu Glu Asn Phe Arg
        275                 280                 285

Val Gly Met Ser Val Leu Val Thr Ile Lys Pro His His His His His
    290                 295                 300

His
305
```

<210> SEQ ID NO 19
<211> LENGTH: 464
<212> TYPE: PRT
<213> ORGANISM: Artificial Sequence
<220> FEATURE:
<223> OTHER INFORMATION: aa 21-477 of jhp_0552 + C-terminal His-tag

<400> SEQUENCE: 19

```
Met Gln Thr Pro Ser Lys Thr Pro Asp Glu Ile Lys Gln Ile Leu Asn
1               5                   10                  15

Asn Tyr Ser His Lys Asn Leu Lys Leu Ile Asp Pro Pro Thr Ser Ser
            20                  25                  30

Leu Glu Ala Thr Pro Gly Phe Leu Pro Ser Pro Lys Glu Thr Ala Thr
        35                  40                  45

Thr Ile Asn Gln Glu Ile Ala Lys Tyr His Glu Lys Ser Asp Lys Ala
    50                  55                  60

Ala Leu Gly Leu Tyr Glu Leu Leu Lys Gly Ala Thr Thr Asn Leu Ser
65                  70                  75                  80

Leu Gln Ala Gln Glu Leu Ser Val Lys Gln Ala Met Lys Asn His Thr
                85                  90                  95

Ile Ala Lys Ala Met Phe Leu Pro Thr Leu Asn Ala Ser Tyr Asn Phe
            100                 105                 110

Lys Asn Glu Ala Arg Asp Thr Pro Glu Tyr Lys His Tyr Asn Thr Gln
        115                 120                 125

Gln Leu Gln Ala Gln Val Thr Leu Asn Val Phe Asn Gly Phe Ser Asn
    130                 135                 140

Val Asn Asn Val Lys Glu Lys Ser Ala Thr Tyr Arg Ser Thr Val Ala
145                 150                 155                 160

Asn Leu Glu Tyr Ser Arg Gln Ser Val Tyr Leu Gln Val Val Gln Gln
                165                 170                 175

Tyr Tyr Glu Tyr Phe Asn Asn Leu Ala Arg Met Ile Ala Leu Gln Lys
            180                 185                 190

Lys Leu Glu Gln Ile Gln Thr Asp Ile Lys Arg Val Thr Lys Leu Tyr
        195                 200                 205

Asp Lys Gly Leu Thr Thr Ile Asp Asp Leu Gln Ser Leu Lys Ala Gln
    210                 215                 220

Gly Asn Leu Ser Glu Tyr Asp Ile Leu Asp Met Gln Phe Ala Leu Glu
225                 230                 235                 240

Gln Asn Arg Leu Thr Leu Glu Tyr Leu Thr Asn Leu Ser Val Lys Asn
                245                 250                 255

Leu Lys Lys Thr Thr Ile Asp Ala Pro Asn Leu Gln Leu Arg Glu Arg
            260                 265                 270

Gln Asp Leu Val Ser Leu Arg Glu Gln Ile Ser Ala Leu Arg Tyr Gln
        275                 280                 285

Asn Lys Gln Leu Asn Tyr Tyr Pro Lys Ile Asp Val Phe Asp Ser Trp
    290                 295                 300

Leu Phe Trp Ile Gln Lys Pro Tyr Ala Thr Gly Arg Phe Gly Asn
305                 310                 315                 320

Phe Tyr Pro Gly Gln Gln Asn Thr Ala Gly Val Thr Ala Thr Leu Asn
                325                 330                 335

Ile Phe Asp Asp Ile Gly Leu Ser Gln Lys Gln Ser Ile Met Leu
            340                 345                 350

Gly Gln Leu Ala Asn Glu Lys Asn Leu Ala Tyr Lys Lys Leu Glu Gln
        355                 360                 365

Glu Lys Asp Glu Gln Leu Tyr Arg Lys Ser Leu Asp Ile Ala Arg Ala
```

```
            370                 375                 380
Lys Ile Glu Ser Ser Lys Ala Ser Leu Asp Ala Ala Asn Leu Ser Phe
385                 390                 395                 400

Ala Asn Ile Lys Arg Lys Tyr Asp Ala Asn Leu Val Asp Phe Thr Thr
                405                 410                 415

Tyr Leu Arg Gly Leu Thr Thr Arg Phe Asp Ala Glu Val Ala Tyr Asn
                420                 425                 430

Leu Ala Leu Asn Asn Tyr Glu Val Gln Lys Ala Asn Tyr Ile Phe Asn
                435                 440                 445

Ser Gly His Lys Ile Asp Asp Tyr Val His His His His His His
                450                 455                 460

<210> SEQ ID NO 20
<211> LENGTH: 507
<212> TYPE: PRT
<213> ORGANISM: Artificial Sequence
<220> FEATURE:
<223> OTHER INFORMATION: full-length jhp_0305 + C-terminal His-tag

<400> SEQUENCE: 20

Met Lys Met Ile Leu Phe Asn Gln Asn Pro Met Ile Glu Lys Leu Leu
1               5                   10                  15

Glu Ser Val Ser Lys Lys Leu Glu Leu Ser Ile Glu Asn Phe Asn His
                20                  25                  30

Tyr Gln Glu Leu Ser Ala Arg Leu Lys Gly Asp Pro Glu Trp Leu Leu
            35                  40                  45

Ile Ala Asp Asp Glu Cys Leu Glu Lys Leu Asp Gln Val Asp Trp Leu
50                  55                  60

Glu Leu Lys Glu Thr Ile Ser Gln Asn Lys Asn Ser Val Cys Met Tyr
65                  70                  75                  80

Lys Lys Gly Asn Glu Ala Gln Pro Phe Leu Glu Gly Phe Glu Met Lys
                85                  90                  95

Ile Lys Lys Pro Phe Leu Pro Thr Glu Met Leu Lys Val Leu Gln Lys
            100                 105                 110

Lys Leu Gly Ser Asn Ala Ser Glu Leu Glu Pro Ser Gln Asn Leu Asp
        115                 120                 125

Pro Thr Gln Glu Ile Leu Glu Thr Asn Trp Asp Glu Leu Glu Asn Leu
130                 135                 140

Gly Asp Leu Glu Ala Leu Ala Lys Glu Glu Pro Asn Asn Glu Glu Gln
145                 150                 155                 160

Leu Leu Pro Thr Leu Asn Glu Gln Glu Gly Glu Thr Pro Lys Glu Glu
                165                 170                 175

Ala Gln Glu Glu Val Lys Lys Glu Glu Val Lys Glu Met Gln Glu Glu
            180                 185                 190

Val Lys Glu Lys Gln Lys Gln Glu Val Ala Glu Asn Pro Gln Asp Glu
        195                 200                 205

Glu Lys Pro Lys Asp Asp Glu Thr Gln Gly Ser Val Glu Pro Pro Lys
210                 215                 220

Asp Glu Glu Val Ser Lys Glu Leu Glu Thr Gln Glu Glu Leu Glu Thr
225                 230                 235                 240

Pro Lys Glu Glu Thr Gln Glu Glu Pro Ile Lys Glu Glu Thr Gln
                245                 250                 255

Glu Ile Lys Glu Glu Lys Gln Glu Lys Thr Gln Asp Ser Pro Ser Ala
            260                 265                 270

Gln Glu Leu Glu Ala Met Gln Glu Leu Val Lys Glu Ile Gln Glu Asn
```

```
                275                 280                 285
Ser Asn Asp Gln Glu Asn Lys Lys Glu Thr Gln Glu Thr Gln Glu Asn
            290                 295                 300

Thr Glu Thr Pro Gln Asp Ile Glu Thr Gln Glu Leu Glu Ile Pro Lys
305                 310                 315                 320

Glu Glu Glu Thr Gln Glu Val Ala Glu Thr Gln Val Gln Gly Leu
                325                 330                 335

Glu Lys Glu Glu Ile Ala Glu Thr Pro Gln Lys Glu Ile Gln Glu
            340                 345                 350

Thr Gln Asp Glu Thr Pro Gln Glu Leu Glu Ala Gln Asp Glu Lys Leu
            355                 360                 365

Gln Glu Asn Glu Thr Pro Lys Asp Glu Ser Met Gln Glu Ser Ala Gln
            370                 375                 380

Asn Leu Gln Asp Lys Glu Thr Pro Gln Glu Thr Gln Glu Asp His
385                 390                 395                 400

Tyr Glu Ser Ile Glu Asp Ile Pro Glu Pro Val Met Ala Lys Ala Met
                405                 410                 415

Gly Glu Glu Leu Pro Phe Leu Asn Glu Ala Val Ala Lys Ile Pro Asn
            420                 425                 430

Asn Glu Asn Asp Thr Glu Thr Pro Lys Glu Ser Asp Ile Lys Ala Pro
            435                 440                 445

Gln Glu Lys Glu Glu Ser Asp Lys Thr Ser Ser Pro Leu Glu Leu Arg
    450                 455                 460

Leu Asn Leu Gln Asp Leu Leu Lys Ser Leu Asn Gln Glu Ser Leu Lys
465                 470                 475                 480

Ser Leu Leu Glu Asn Lys Thr Leu Ser Ile Lys Ile Thr Leu Glu Asp
                485                 490                 495

Lys Lys Pro Asn Glu His His His His His
            500                 505

<210> SEQ ID NO 21
<211> LENGTH: 201
<212> TYPE: PRT
<213> ORGANISM: Artificial Sequence
<220> FEATURE:
<223> OTHER INFORMATION: full-length clpP + C-terminal His-tag

<400> SEQUENCE: 21

Met Gly Tyr Ile Pro Tyr Val Ile Glu Asn Thr Glu Arg Gly Glu Arg
1               5                   10                  15

Ser Tyr Asp Ile Tyr Ser Arg Leu Leu Lys Asp Arg Ile Val Leu Leu
            20                  25                  30

Ser Gly Glu Ile Asn Asp Ser Val Ala Ser Ser Ile Val Ala Gln Leu
        35                  40                  45

Leu Phe Leu Glu Ala Glu Asp Pro Glu Lys Asp Ile Gly Leu Tyr Ile
    50                  55                  60

Asn Ser Pro Gly Gly Val Ile Thr Ser Gly Leu Ser Ile Tyr Asp Thr
65                  70                  75                  80

Met Asn Phe Ile Arg Pro Asp Val Ser Thr Ile Cys Ile Gly Gln Ala
                85                  90                  95

Ala Ser Met Gly Ala Phe Leu Leu Ser Cys Gly Ala Lys Gly Lys Arg
            100                 105                 110

Phe Ser Leu Pro His Ser Arg Ile Met Ile His Gln Pro Leu Gly Gly
        115                 120                 125

Ala Gln Gly Gln Ala Ser Asp Ile Glu Ile Ile Ser Asn Glu Ile Leu
```

```
                130               135                140
Arg Leu Lys Gly Leu Met Asn Ser Ile Leu Ala Gln Asn Ser Gly Gln
145                 150                 155                 160

Ser Leu Glu Gln Ile Ala Lys Asp Thr Asp Arg Asp Phe Tyr Met Ser
                165                 170                 175

Ala Lys Glu Ala Lys Glu Tyr Gly Leu Ile Asp Lys Val Leu Gln Lys
            180                 185                 190

Asn Val Lys His His His His His His
            195                 200

<210> SEQ ID NO 22
<211> LENGTH: 528
<212> TYPE: DNA
<213> ORGANISM: Artificial Sequence
<220> FEATURE:
<223> OTHER INFORMATION: aa 34-201 of jhp_0775 + C-terminal His-tag

<400> SEQUENCE: 22
atgcagctaa tcccccttc agctaacggg ttgcaagccc ccatttatcc cccaaccaat     60 ttcacccca gaaagagcat tcagcctctc ccaagccctc gccttgagaa taacgatcag    120
cccatcatta gctctaatcc cactaacgct atccctaaca cccccattct cacgcccaat   180
aatgtcattg agttgaatgc ggtgggcatg ggtgtggctc cagaatccac catttcgccc   240
tctcaagctc tagctttagc taagcgagcg gctattgttg atggctaccg ccagttgggt   300
gaaaaaatgt atggcatcag agtgaacgct caagacaccg tcaaagacat ggttttacaa   360
aattccgtga ttaaaacgag agtgaatgcc ctcattcgta acgctgaaat cactgagact   420
atctataaag acggcttgtg ccaggtaagc atggagctta aattagacgg caggatttgg   480
tatcgtattt tgagcggatc gagaggacac catcatcatc atcattaa                528

<210> SEQ ID NO 23
<211> LENGTH: 813
<212> TYPE: DNA
<213> ORGANISM: Artificial Sequence
<220> FEATURE:
<223> OTHER INFORMATION: aa 23-285 of jhp_0119 + C-terminal His-tag

<400> SEQUENCE: 23
atgactatta acactacagt tgatcccaat gttatgtttt ctgaaagctc cacagggaat     60
gtgaaaaaag accgcaagag ggttttaaag agcatggttg atttagaaaa agagcgcgtg    120
aagaatttta accagtattc tgaaaccaag atgagtaagg gcgatttatc cgcttttgga    180 gcttttcttta aggggagttt ggaagattgc gtggagcaaa agatttgtta ctatgagcat    240
aggaatggca aggtttcttt tgtggtgaat gacagagaaa agttttataa gcatgtgctt    300
aaagacttag ggacagagct ttcactcccc ttgttcaact ggctttacaa aggctcagat    360 tttgggggctt tgcatgagca gtttggggac atgtatgatg ggtatatcaa atacttgatc    420
agcatggtta gggtgagcca aaaagaaaag gctagaaaag tggatgcaat cgttcttaaa    480
aaaatggaag aacaagctga aaagacact aaggcagcat tccaaaagag gagcagtggg    540
gagcttgaaa gccatactga tagccctgaa tttataagct cttctaagac acagaattct    600
tctaacccag atctagaccc tatgactaac gctaacacgc tcaaagaaac agcttcaaaa    660
gagccagaga cttcttcaaa aaaggaaaaa aagcccaaga aaaacgacg cctttcaaag    720 aaagaaaagc aacaacaggc cttacaacaa gagtttgaaa gcaaattag cgactctagt    780 aagtctgaaa acaccatca tcatcatcat taa                                  813
```

<210> SEQ ID NO 24
<211> LENGTH: 699
<212> TYPE: DNA
<213> ORGANISM: Artificial Sequence
<220> FEATURE:
<223> OTHER INFORMATION: aa 44-268 of jhp_0173 + C-terminal His-tag

<400> SEQUENCE: 24

```
atgaaaagca ccagagtcgc tcctaaagag acttttttac aaaccgatag tggcatgcaa      60
aaaataggca acactaaaga tgagaaaaaa gacgatgagt ttgaaagctt gaatatggat     120
tctcccaaac aagaagacaa gttagacaaa gtggtggata atattaaaaa acaagagagt     180
gaaaattcta tgcccattca aaccgatcaa gctcaaatgg agatgaaaac aacagaagaa     240
aaacaagaat ctcaaaaaga attaaaagct gttgagccta ttcccatgag cactcaaaaa     300
gaatctcagg ctgtggctaa aaaagaaacc ccccataaaa agcctaaagt agcgccaaaa     360
gataaagaag cgcataaaga taaagctaag catgcagcta aagagccaaa agtcaaaaaa     420
gaagctcgta agaagtttc taagaaagct aattctaaaa ccaatcttac taaagggcat     480
tatttgcaag tggggttttt tgcgcacacg cccaacaaag ccttttttaca agagtttaat     540
caattccccc ataaaattga agataggggg gctactaaac gctacctcat aggcccttat     600
aagagcaagc aagaagcctt aatgcatgcc gatgaagtca gcaagaagat gactaaaccg     660
gttgtcatag aagtgcggca ccatcatcat catcattaa                            699
```

<210> SEQ ID NO 25
<211> LENGTH: 918
<212> TYPE: DNA
<213> ORGANISM: Artificial Sequence
<220> FEATURE:
<223> OTHER INFORMATION: aa 32-329 of jhp_1381 + C-terminal His-tag

<400> SEQUENCE: 25

```
atgcgcccta aggctgaagt gttgcaaggg ttttagagg ctagggaata cagcgtgagc      60
tctaaagtcc ctggccgcat tgaaaaggtg tttgttaaaa aaggcgatcg cattaaaaag     120
ggcgatttag ttttagcat ttctagccct gaattagaag ccaagctcgc tcaagctgaa     180
gccgggcata agccgctaa agccgttagc gatgaagtga aaagaggctc aagagatgaa     240
acgatcaatt ctgcgaggga cgtttggcaa gcggcaaaat cccaagcgaa tttggctaaa     300
gagacttata gcgcgttca agatttgtat gacaatggcg tggcgagttt gcaaaagcgc     360
gatgaagcct atgcggctta tgaaagcacc aaatacaacg agagcgcggc ttaccaaaag     420
tataaaatgg ctttagggg ggcgagttct gaaagcaaga ttgccgctaa ggctaaagag     480
agcgcggctt tagggcaagt gaatgaagtg gaatcctact aaaagacgt caaagcccta     540
gcccctattg atggggaagt gagtaacgtg cttttaagcg gtggcgagct tagccctaag     600
ggctttcctg tggtgctcat gatagattta aaggatagtg ggttaaaaat cagcgtgcct     660
gaaaagtatt tgaacgagtt taaagtgggt aaggaattg aaggctatat cccagcgttg     720
aaaagaagcg cgaaattcag ggtcaaatat ttgagcgtga tggggatttt tgcgacctgg     780
aaagcgacga taattccaa cacttacgac atgaaaagct atgaagtgga ggccataccc     840
ttagaagagt tggaaaactt tagggtgggg atgagcgtgt tggttaccat taaacctcac     900
catcatcatc atcattaa                                                   918
```

<210> SEQ ID NO 26

<211> LENGTH: 1395
<212> TYPE: DNA
<213> ORGANISM: Artificial Sequence
<220> FEATURE:
<223> OTHER INFORMATION: aa 21-477 of jhp_0552 + C-terminal His-tag

<400> SEQUENCE: 26

| | | |
|---|---|---|
| atgcaaaccc cctctaaaac ccctgatgaa atcaagcaaa tccttaacaa ttatagccat | 60 |
| aagaatttaa agctcattga tccgccgaca agttctttag aagcgacacc gggtttttta | 120 |
| ccctcgccta agaaacagc gaccacgatc aatcaagaga tcgctaaata ccatgaaaaa | 180 |
| agcgataaag ccgctttggg gctttatgaa ttgctaaagg gggctaccac caatctcagt | 240 |
| ttgcaagcgc aagaactcag tgtcaagcaa gcgatgaaga accacaccat cgccaaagcg | 300 |
| atgttttgc ctactttgaa cgcgagttat aattttaaaa atgaagctag ggatactcca | 360 |
| gaatataagc attataacac ccaacaactc caagctcaag tcacattgaa tgtgtttaat | 420 |
| ggctttagca atgtgaataa tgtcaaagaa agtctgccga cttaccgatc cactgtggct | 480 |
| aatttagaat atagccgcca aagcgtgtat ttgcaagtgg tgcaacaata ctacgagtat | 540 |
| tttaacaatc tcgctcgcat gatcgctttg caaagaaat tagagcaaat ccaaacggac | 600 |
| attaaaaggg ttactaagct ctatgacaaa gggctgacca cgattgatga tttacaaagc | 660 |
| ttaaaagcgc aagggaattt gagcgaatac gatattttgg acatgcaatt tgctttggag | 720 |
| caaaaccgct tgactttaga aaccctcact aacctcagtg tgaaaaattt gaaaagacc | 780 |
| acgattgatg cgcctaattt gcaattaaga gaaaggcagg atttggtttc tttaagggag | 840 |
| cagatttctg cactcagata ccaaaacaag caactcaatt attaccccaa gatagatgtg | 900 |
| tttgactcat ggctttttg gatccaaaaa cccgcttatg ccacagggcg ttttgggaat | 960 |
| ttctacccag gtcagcaaaa tacggctggg gttactgcga ctttgaatat ttttgatgat | 1020 |
| ataggggttga gcttgcaaaa acaatccatc atgctaggcc aattagcgaa tgaaaagaat | 1080 |
| ttagcgtata aaaaattgga gcaagaaaaa gacgaacagc tttacagaaa gtcgcttgat | 1140 |
| attgccagag ctaagattga atcttcaaag gctagtttgg atgcggccaa tctttcttt | 1200 |
| gccaatatta aaggaaata cgacgctaat ttagtggatt tcactaccta tttaaggggc | 1260 |
| ttaaccacgc gctttgatgc agaagtggct tacaatttag cgctcaacaa ttacgaagtg | 1320 |
| caaaaagcca attacattt taacagcggg cataaaatag acgactatgt gcatcaccat | 1380 |
| catcatcatc attaa | 1395 |

<210> SEQ ID NO 27
<211> LENGTH: 1524
<212> TYPE: DNA
<213> ORGANISM: Artificial Sequence
<220> FEATURE:
<223> OTHER INFORMATION: full-length jhp_0305 + C-terminal His-tag
    (codon-optimized)

<400> SEQUENCE: 27

| | | |
|---|---|---|
| atgaaaatga tcctgttcaa ccagaacccg atgatcgaaa aactgctgga atctgtttct | 60 |
| aaaaaactgg aactgtctat cgaaaacttc aaccactacc aggaactgtc tgctcgtctg | 120 |
| aaaggtgacc ggaatggct gctgatcgct gacgacgaat gcctggaaaa actggaccag | 180 |
| gttgactggc tggaactgaa agaaaccatc tctcagaaca aaaactctgt tgcatgtac | 240 |
| aaaaaaggta cgaagctca gccgttcctg aaggtttcg aatgaaaat caaaaaccg | 300 |
| ttcctgccga ccgaaatgct gaaagttctg cagaaaaaac tgggttctaa cgcttctgaa | 360 |

```
ctggaaccgt ctcagaacct ggacccgacc caggaaatcc tggaaaccaa ctgggacgaa    420
ctggaaaacc tgggtgacct ggaagctctg gctaaagaag aaccgaacaa cgaagaacag    480
ctgctgccga ccctgaacga acaggaaggt gaaaccccga agaagaagc tcaggaagaa    540 gttaaaaaag aagaagttaa agaaatgcag gaagaagtta agaaaaaaca gaaacaggaa    600
gttgctgaaa acccgcagga cgaagaaaaa ccgaaagacg acgaaaccca gggttctgtt    660
gaaccgccga agacgaaga agtttctaaa gaactggaaa cccaggaaga actggaaacc    720
ccgaaagaag aaacccagga acaggaaccg atcaaagaag aaacccagga aatcaaagaa    780
gaaaaacagg aaaaaaccca ggactctccg tctgctcagg aactggaagc tatgcaggaa    840
ctggttaaag aaatccagga aaactctaac gaccaggaaa acaaaaaaga aacccaggaa    900
acccaggaaa acaccgaaac cccgcaggac atcgaaaccc aggaactgga aatcccgaaa    960
gaagaagaaa cccaggaagt tgctgaaaaa acccaggttc agggtctgga aaagaagaa    1020 atcgctgaaa ccccgcagga aaagaaatc caggaaaccc aggacgaaac cccgcaggaa    1080
ctggaagctc aggacgaaaa actgcaggaa acgaaaccc gaaagacga atctatgcag    1140 gaatctgctc agaacctgca ggacaaagaa ccccgcagg aagaaaccca ggaagaccac    1200
tacgaatcta tcgaagacat cccggaaccg gttatggcta aagctatggg tgaagaactg    1260
ccgttcctga cgaagctgt tgctaaaatc ccgaacaacg aaaacgacac cgaaaccccg    1320
aaagaatctg acatcaaagc tccgcaggaa aaagaagaat ctgacaaaac ctcttctccg    1380
ctggaactgc gtctgaacct gcaggacctg ctgaaatctc tgaaccagga atctctgaaa    1440
tctctgctgg aaaacaaaac cctgtctatc aaaatcaccc tggaagacaa aaaaccgaac    1500
gaacaccatc atcatcatca ttaa                                           1524
```

<210> SEQ ID NO 28
<211> LENGTH: 606
<212> TYPE: DNA
<213> ORGANISM: Artificial Sequence
<220> FEATURE:
<223> OTHER INFORMATION: full-length clpP + C-terminal His-tag

<400> SEQUENCE: 28

```
atgggataca ttccttatgt aatagaaaat acagagcgtg gcgaacgcag ttatgatatt     60
tactcacgcc ttttaaagga tcgcatcgtt ttattgagcg gtgagattaa cgatagcgtg    120
gcgtcttcta tcgtggccca actcttgttt ttggaagccg aagatcctga aaaagacatt    180
ggcttgtata tcaattctcc cggtgggggtg ataacgagcg gtcttagcat ttatgacacc    240 atgaattta tccgccctga tgtttccacg atttgcatcg gtcaagcggc ttctatgggg    300 gcgttttttac taagctgtgg ggctaagggc aagcgcttt cactgcccca ttcaaggatt    360
atgatccacc agcctttagg ggggggctcaa gggcaagcga gcgatattga aatcatttct    420
aacgagatcc ttaggcttaa gggtttgatg aattctattt tggctcaaaa ctcagggcag    480
agtttggagc aaatcgctaa agacacggat agggattttt acatgagcgc taaagaagct    540
aaagagtatg gcttgattga taaagtgtta cagaaaaacg tgaagcacca tcatcatcat    600
cattaa                                                               606
```

<210> SEQ ID NO 29
<211> LENGTH: 12
<212> TYPE: PRT
<213> ORGANISM: Artificial Sequence
<220> FEATURE:
<223> OTHER INFORMATION: targeting peptide

```
<400> SEQUENCE: 29

Asn Trp Tyr Leu Pro Trp Leu Gly Thr Asn Asp Trp
1               5                   10
```

HELICOBACTER PYLORI VACCINES

CROSS-REFERENCE TO RELATED APPLICATIONS

This patent application is the U.S. national phase of International Application No. PCT/EP2016/080878, filed on Dec. 14, 2016, which claims the benefit of European Patent Application No. 15199862.2, filed Dec. 14, 2015, the disclosures of which are incorporated herein by reference in their entireties for all purposes.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 58,992 byte ASCII (Text) file named "50-18US ST25.txt", created on Jun. 13, 2018.

TECHNICAL FIELD OF THE INVENTION

The present invention relates to immunogenic compositions and their use in the prevention or treatment of diseases or disorders caused by or associated with *Helicobacter pylori*, in particular *H. pylori* infection and gastroduodenal disorders caused by *H. pylori*. The present invention further relates to methods of detecting *H. pylori* infection in a subject.

BACKGROUND OF THE INVENTION

*Helicobacter pylori* (*H. pylori*) is a microaerophilic gram-negative bacterium, able to persist lifelong in the human stomach. The *H. pylori* infection is the most common bacterial infectious disease in humans: half of the worldwide population is infected with *H. pylori*, depending on the socioeconomic status of the region (Perez-Perez et al., 2004). The infection is associated with numerous gastric diseases such as chronic atrophic gastritis, peptic ulcers, stomach or gastric cancer and the mucosa associated lymphoid tissue (MALT) lymphoma (Nomura et al., 1994; Forman, 1996; Parsonnet et al., 1991; Blaser et al., 1995). *H. pylori* is the main cause of gastric cancer—the third most common type of cancer with 983.000 cases world-wide in 2011 (Jemal et al., 2011).

Gastric cancer is associated with considerable socio-economic costs. Treating a single patient with gastric cancer currently costs about EUR 50,000. Prevention of gastric cancer includes early treatment of infection caused by *H. pylori*. According to estimates, at least one third of individuals with an infection caused by *H. pylori* require treatment. At present, it is difficult to predict which patients will develop the subsequent diseases associated with an *H. pylori* infection. Based on the results of numerous studies, general treatment of the *H. pylori* infection to prevent gastric carcinoma is cost efficient, as it would prevent over 95% of cases (Graham & Shiotani, 2005). Therapy is clearly indicated for patients with gastric ulcers, precancerous or definitive gastric cancer, relatives of gastric cancer patients, as well as patients requiring long-term therapy with non-steroidal anti-inflammatory drugs (including aspirin for cardiovascular diseases). Due to high gastric cancer rates in Japan, the treatment of all individuals infected with *H. pylori* is recommended there, despite steadily increasing antibiotic resistance rates (Shiota et al., 2010).

The standard therapy of infections caused by *H. pylori* to date consists of two antibiotics combined with a proton pump inhibitor such as omeprazole. The cost of a one-week treatment is approximately EUR 200 per patient. This therapy has significant side effects in some patients and leads to a steep increase in resistant pathogens. Because second- and third-line therapies often fail, more than 10% of all patients can no longer be treated (Gao et al., 2010), which could rise to an estimated 60% by 2020. If a vaccine against *H. pylori* were available, it would benefit millions of patients and reduce healthcare costs significantly. Vaccines are highly effective in combating prevalent infectious diseases. In fact, the U.S. Center of Disease Control called vaccination the most effective method for preventing infectious diseases (U.S. CDC, 2011). However, to date, there is no effective vaccine for humans against *H. pylori* available. The Phase II clinical trial Novartis completed in 2010, using a *H. pylori* vaccine based on three antigens (CagA, VacA, NapA), was considered unsuccessful. As these antigens are very variable and are prevalent in only some of the *H. pylori* strains, only partial protection was to be expected.

Accordingly, it was an object of the present invention to identify polypeptides of *H. pylori* that elicit an immune response in a subject and that are suitable as pan-protective vaccines against *H. pylori*. It was a further object of the present invention to provide immunogenic compositions comprising one or more of these polypeptides/antigens, which compositions can be used for the prevention or treatment of diseases or disorders caused by or associated with *H. pylori*. It was yet another object of the present invention to identify polypeptides/antigens that can be used as biomarkers for *H. pylori* infection and to provide methods for detecting *H. pylori* infection in a subject based on their use.

SUMMARY OF THE INVENTION

In one aspect, the present invention relates to an immunogenic composition comprising
(a) at least one isolated (poly-)peptide comprising (i) an amino acid sequence selected from the group consisting of SEQ ID NOs: 1 to 7; or (ii) an immunogenic variant of (i); or (iii) an immunogenic fragment of (i) or (ii); or
(b) at least one nucleic acid molecule encoding an isolated (poly-)peptide according to item (a).

In one embodiment, the isolated (poly-)peptide is a recombinant (poly-)peptide.

In one embodiment, the immunogenic fragment comprises an extracellular domain or a fragment thereof.

In one embodiment, the immunogenic variant comprises an amino acid sequence which is at least 60%, at least 70%, at least 80%, at least 90%, at least 95% or at least 97% identical to an amino acid sequence selected from the group consisting of SEQ ID NOs: 1 to 7.

In one embodiment, the immunogenic composition further comprises at least one additional antigen from *H. pylori*, wherein, preferably, the additional antigen is selected from the group consisting of outer membrane proteins and virulence factor proteins of *H. pylori*, immunogenic fragments thereof and nucleic acid molecules encoding these proteins or fragments.

In one embodiment, the isolated (poly-)peptide is a fusion protein.

In one embodiment, the fusion protein comprises
(i) a first amino acid sequence selected from the group consisting of SEQ ID NOs: 1 to 7 or an immunogenic variant thereof or an immunogenic fragment of any of the foregoing and a second, preferably different, amino acid sequence selected from the group consisting of SEQ ID NOs: 1 to 7 or an immunogenic variant thereof or an immunogenic fragment of any of the foregoing; or (ii) an amino acid sequence selected from the group consisting of SEQ ID NOs: 1 to 7 or an immunogenic variant thereof or an immunogenic fragment of any of the foregoing and at least one additional antigen from *H. pylori*, wherein, preferably, the additional antigen is selected from the group consisting of outer membrane proteins and virulence factor proteins of *H. pylori* and immunogenic fragments thereof; or (iii) a first amino acid sequence selected from the group consisting of SEQ ID NOs: 1 to 7 or an immunogenic variant thereof or an immunogenic fragment of any of the foregoing, a second, preferably different, amino acid sequence selected from the group consisting of SEQ ID NOs: 1 to 7 or an immunogenic variant thereof or an immunogenic fragment of any of the foregoing, and at least one additional antigen from *H. pylori*, wherein, preferably, the additional antigen is selected from the group consisting of outer membrane proteins and virulence factor proteins of *H. pylori* and immunogenic fragments thereof.

In one embodiment, the immunogenic composition comprises at least two different isolated (poly-)peptides according to item (a) or at least two different nucleic acid molecules according to item (b).

In one embodiment, the nucleic acid molecule is DNA or RNA, wherein, preferably, the nucleic acid molecule is contained in a vector.

In one embodiment, the immunogenic composition further comprises at least one adjuvant.

In one embodiment, the immunogenic composition is a vaccine.

In a further aspect, the present invention relates to an immunogenic composition as defined herein for use as a medicament.

In yet another aspect the present invention relates to an immunogenic composition as defined herein or to a polypeptide ligand specifically binding to an isolated (poly-)peptide according to item (a) for use in a method of preventing or treating a disease or disorder caused by or associated with *H. pylori*, wherein, preferably, the disease or disorder is selected from the group consisting of *H. pylori* infection and gastroduodenal disorders caused by *H. pylori*.

In a further aspect, the present invention relates to the use of an immunogenic composition as defined herein or of a polypeptide ligand specifically binding to an isolated (poly-)peptide according to item (a) in the manufacture of a medicament for preventing or treating a disease or disorder caused by or associated with *H. pylori*, wherein, preferably, the disease or disorder is selected from the group consisting of *H. pylori* infection and gastroduodenal disorders caused by *H. pylori*.

In another aspect, the present invention relates to a method of preventing or treating a disease or disorder caused by or associated with *H. pylori*, wherein, preferably, the disease or disorder is selected from the group consisting of *H. pylori* infection and gastroduodenal disorders caused by *H. pylori*, the method comprising administering an immunogenic composition as defined herein or a polypeptide ligand specifically binding to an isolated (poly-)peptide according to item (a) to a subject in need thereof.

In one embodiment, the gastroduodenal disorders are selected from the group consisting of gastritis, chronic gastritis, gastric or duodenal ulcer, stomach cancer and MALT lymphoma.

In another aspect, the present invention relates to a kit comprising an immunogenic composition as defined herein.

In another aspect, the present invention relates to a method of detecting *H. pylori* infection in a subject, comprising the steps of:
(a) providing at least one isolated (poly-)peptide as defined herein, wherein, preferably, the at least one isolated (poly-)peptide is immobilized on a solid support;
(b) contacting the at least one isolated (poly-)peptide with a biological sample obtained from the subject; and
(c) determining the presence or absence of antibodies specifically binding to the at least one isolated (poly-)peptide in the biological sample,
wherein the presence of antibodies indicates *H. pylori* infection in the subject.

In yet another aspect, the present invention relates to the use of a (poly-)peptide comprising (i) an amino acid sequence selected from the group consisting of SEQ ID NOs: 1 to 7; or (ii) an immunogenic variant of (i); or (iii) an immunogenic fragment of (i) or (ii), or of an antibody specifically binding to the (poly-)peptide as a biomarker for *H. pylori* infection.

In another aspect, the present invention relates to a kit comprising at least one isolated (poly-) peptide as defined herein, preferably a plurality of different isolated (poly-)peptides as defined herein.

In one embodiment, the at least one isolated (poly-)peptide as defined herein or the plurality of different isolated (poly-)peptides as defined herein is/are immobilized on a solid support.

In yet another aspect, the present invention relates to the use of a kit as defined above for detecting *H. pylori* infection in a subject.

DETAILED DESCRIPTION OF THE INVENTION

Figure 1:
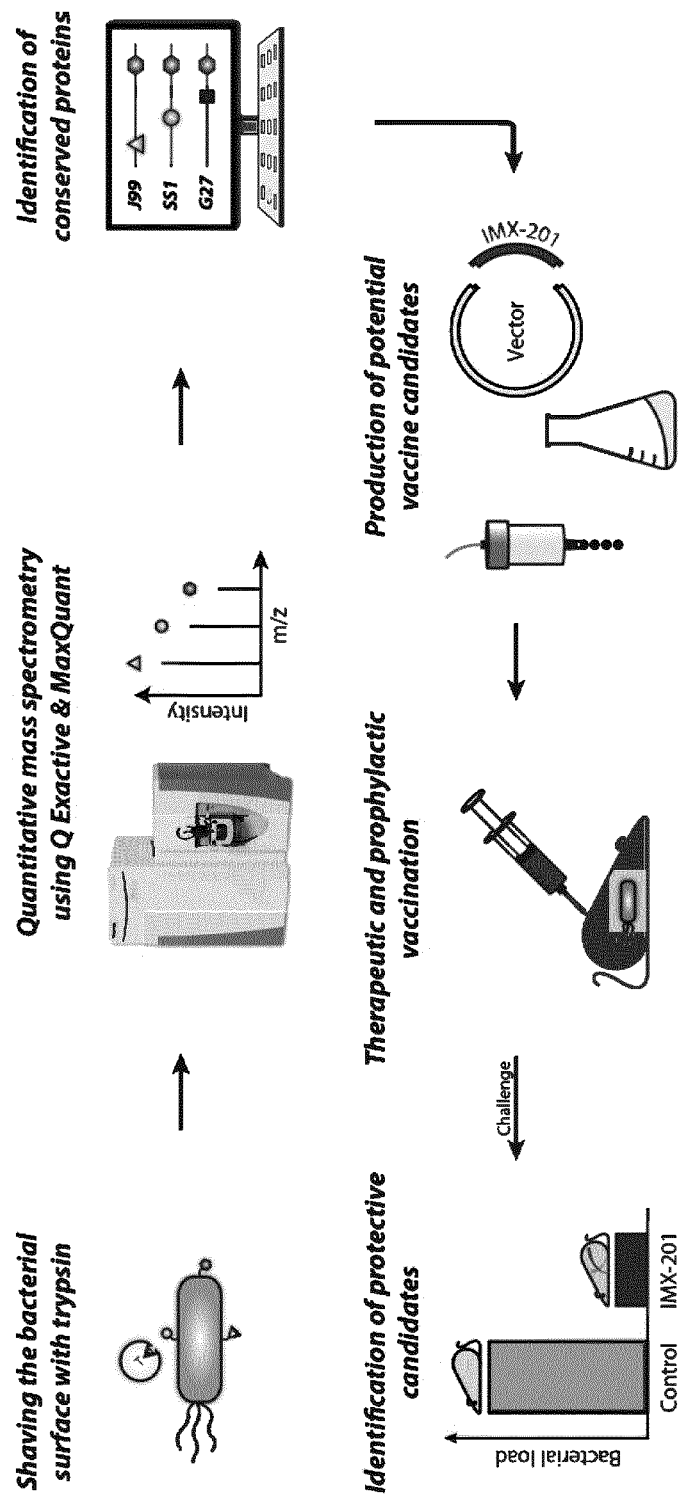
FIG. 1 is a scheme illustrating the identification of vaccine candidates by surfome shaving.

Although the present invention is described in detail above and below, it is to be understood that this invention is not limited to the particular methodologies, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

In the following, certain elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, $3^{rd}$ Edition, J. Sambrook et al. eds., Cold Spring Harbor Laboratory Press, Cold Spring Harbor 2000).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The inventors have used a surfome shaving approach to identify proteins as suitable vaccine candidates against *H. pylori*. The proteins are putative outer membrane proteins (OMPs), which are usually attractive targets for the immune system. They were cloned, recombinantly produced in *E. coli*, purified, and successfully tested for eliciting a humoral immune response in mice. In view of their high conservation in *H. pylori*, the proteins are expected to confer pan-protective immunity against *H. pylori*.

The present invention provides an immunogenic composition comprising (a) at least one isolated (poly-)peptide comprising or consisting of (i) an amino acid sequence selected from the group consisting of SEQ ID NOs: 1 to 7; or (ii) an immunogenic variant thereof (i.e., an immunogenic variant of (i)); or (iii) an immunogenic fragment of (i) or (ii); or (b) at least one nucleic acid molecule encoding an isolated (poly-)peptide according to item (a).

The term "immunogenic", as used herein, is meant to refer to the ability to provoke an immune response, i.e., to induce a humoral and/or cell-mediated immune response, in a subject. A "humoral immune response" is mediated by macromolecules found in extracellular body fluids, such as secreted antibodies, complement proteins and certain antimicrobial peptides. A "cell-mediated immune response" involves the activation of phagocytes, antigen-specific T-lymphocytes and the release of various cytokines in response to an antigen. In one embodiment, the immune response is mediated by antibodies (=antibody response). The term "immunogenic fragment", as used herein, preferably refers to a fragment, which is able to elicit an immune response that is specific to the (poly-)peptide the fragment is derived from.

The term "subject", as used herein, relates to any organism such as vertebrate, particularly any mammal, including both a human and another mammal, e.g. an animal such as a rodent, a rabbit, or a monkey. The rodent may be a mouse, rat, hamster, guinea pig, or chinchilla. Preferably, the subject is a human. In one embodiment, a subject is a subject with or suspected of having a disease, in particular a disease as disclosed herein, also designated "patient" herein.

The term "(poly-)peptide" refers to a molecule which is either a peptide or a polypeptide.

The term "peptide" generally relates to substances which include at least 2, at least 3, at least 4, at least 6, at least 8, at least 10, at least 12 or at least 14 and preferably up to 8, 10, 12, 14, 16, 18, 20, 25, 30, 50, or 100 consecutive amino acids which are connected together by peptide bonds. The terms "polypeptide" and "protein" relate to large peptides, preferably peptides having more than 100 amino acids, but the terms "peptide", "polypeptide" and "protein" are generally used interchangeably herein.

The term "isolated (poly-)peptide" means that the (poly-)peptide is separated from its natural environment. An isolated (poly-)peptide may be in an essentially purified and/or pure state. The term "essentially purified" or "essentially pure" means that the (poly-)peptide is essentially free of other substances, e.g., substances with which it is present and/or associated in nature or in vivo, such as other proteins, nucleic acids, lipids and carbohydrates.

In one embodiment, the isolated (poly-)peptide is a recombinant (poly-)peptide.

The term "recombinant (poly-)peptide", as used herein, is meant to refer to a (poly-)peptide resulting from the expression of recombinant nucleic acid molecules (e.g., DNA) within living cells, e.g. by means of particular expression vectors. Recombinant nucleic acid molecules are nucleic acid molecules formed by laboratory methods of genetic recombination (e.g., molecular cloning).

In one embodiment, the isolated (poly-)peptide is produced in a host cell, preferably a prokaryotic host cell, such as E. coli.

Optionally, the amino acid sequence selected from the group consisting of SEQ ID NOs: 1 to 7 lacks the N-terminal secretion sequence (also referred to herein as signal sequence or signal peptide sequence), e.g., amino acids 1 to 33 of SEQ ID NO: 1, amino acids 1 to 22 of SEQ ID NO: 2, amino acids 1 to 43 of SEQ ID NO: 3, amino acids 1 to 31 of SEQ ID NO: 4 or amino acids 1 to 20 of SEQ ID NO: 5.

In one embodiment, the isolated (poly-)peptide described herein further comprises a detectable label or tag.

The term "detectable label or tag", as used herein, refers to detectable labels or tags allowing the detection and/or isolation and/or immobilization of the isolated (poly-)peptides described herein, and is meant to include any labels/tags known in the art for these purposes. Particularly preferred are affinity tags, such as chitin binding protein (CBP), maltose binding protein (MBP), glutathione-S-transferase (GST), poly(His) (e.g., 6× His or $His_6$), Strep-Tag®, Strep-tag II® and Twin-Strep-tag®; solubilization tags, such as thioredoxin (TRX), poly(NANP) and SUMO; chromatography tags, such as a FLAG-tag; epitope tags, such as V5-tag, myc-tag and HA-tag; fluorescent labels or tags (i.e., fluorochromes/-phores), such as fluorescent proteins (e.g., GFP, YFP, RFP etc.) and fluorescent dyes (e.g., FITC, TRITC, coumarin and cyanine); luminescent labels or tags, such as luciferase; and (other) enzymatic labels (e.g., peroxidase, alkaline phosphatase, β-galactosidase, urease or glucose oxidase). Also included are combinations of any of the foregoing labels or tags.

The amino acid sequence of a (poly)peptidic label or tag may be introduced at any position within the amino acid sequence of the isolated (poly-)peptides described herein. For example, it may be added to their N- and/or C-terminus and/or to an amino acid side chain, e.g., by EDC-NHS coupling to lysines. The same applies to non-peptidic labels or tags.

The isolated (poly-)peptides according to the present invention may further comprise one or more modifications increasing the stability and/or preventing aggregation of the isolated (poly-) peptides. The term "stability" of the isolated (poly-)peptides relates, in particular, to their "half-life", e.g., in vivo. "Half-life" relates to the period of time which is needed to eliminate half of the activity, amount, or number of molecules. Prevention of aggregation will also increase the storage stability of the isolated (poly-)peptides.

The isolated (poly-)peptides may, for example, be fused or conjugated to a half-life extension module. Such modules are known to a person skilled in the art and include, for example, albumin, an albumin-binding domain, an Fc region/domain of an immunoglobulins, an immunoglobulin-binding domain, an FcRn-binding motif, and a polymer. Particularly preferred polymers include polyethylene glycol (PEG), hydroxyethyl starch (HES), hyaluronic acid, poly-sialic acid and PEG-mimetic peptide sequences. Modifications preventing aggregation of the isolated (poly-)peptides are also known to the skilled person and include, for example, the substitution of one or more hydrophobic amino acids, preferably surface-exposed hydrophobic amino acids, with one or more hydrophilic amino acids. In one embodiment, the isolated (poly-) peptide, preferably the amino acid sequence selected from the group consisting of SEQ ID NOs: 1 to 7 or the immunogenic variant thereof or the immunogenic fragment of any of the foregoing, comprises the substitution of up to 10, 9, 8, 7, 6, 5, 4, 3 or 2, preferably 5, 4, 3 or 2, hydrophobic amino acids, preferably surface-exposed hydrophobic amino acids, with hydrophilic amino acids. Preferably, other properties of the isolated (poly-) peptide and/or its above components, e.g., its/their immunogenicity, are not compromised by such substitution.

The isolated (poly-)peptides according to the present invention may also be fused or conjugated to a carrier material, such as Keyhole Limpet Hemocyanin (KLH), BSA, ovalbumin etc., in order to present the respective antigen to the immune system of the subject in a way that allows or promotes the eliciting of an immune response and, in particular, high titer antibodies.

The term "fused to", as used herein, refers, in particular, to genetic fusion, e.g., by recombinant DNA technology.

The term "conjugated to", as used herein, refers, in particular, to chemical and/or enzymatic conjugation resulting in a stable covalent link.

The isolated (poly-)peptides according to the present invention may further comprise an amino acid sequence allowing the targeted delivery of the isolated (poly-)peptides to a given cell, tissue or organ, preferably an amino acid sequence that targets the isolated (poly-)peptides to a particular cell type, e.g., dendritic cells. Suitable amino acid sequences are described, e.g., in Sioud et al., 2013 and Apostolopoulos et al., 2013, and include, for example a peptide with the amino acid sequence NWYLPWLGTNDW (SEQ ID NO: 29).

The terms "part" or "fragment" are used interchangeably herein and refer to a continuous element. For example, a part of a structure, such as an amino acid sequence or protein, refers to a continuous element of said structure. A part or fragment of a protein sequence preferably comprises a sequence of at least 6, in particular at least 8, at least 12, at least 15, at least 20, at least 30, at least 50, at least 100, at least 150, at least 160, at least 170, at least 180, at least 190 or at least 200 consecutive amino acids of the protein sequence.

In embodiments, in which the (poly-)peptide as defined herein comprises an immunogenic fragment of an amino acid sequence selected from the group consisting of SEQ ID NOs: 1 to 7 or of an immunogenic variant thereof, the (poly-)peptide does, preferably, not comprise continuous with the immunogenic fragment further N- and/or C-terminal amino acid sequences of the respective amino acid sequence of SEQ ID NOs: 1 to 7 or of the respective immunogenic variant thereof.

In one embodiment, the immunogenic fragment lacks the N-terminal secretion sequence.

In one embodiment, the immunogenic fragment consists of amino acids 34 to 201 of SEQ ID NO: 1, or amino acids 23 to 285 of SEQ ID NO: 2, or amino acids 44 to 268 of SEQ ID NO: 3, or amino acids 32 to 329 of SEQ ID NO: 4, or amino acids 21 to 477 of SEQ ID NO: 5.

In one embodiment, the immunogenic fragment comprises or consists of an extracellular domain or a fragment thereof. Such sequences/domains may be identified by using standard bioinformatic tools and/or public databases known to a person skilled in the art.

The term "extracellular domain", as used herein, is meant to refer to those parts of a protein that are not cytosolic or embedded in the membrane, and includes parts located/exposed at the surface of the cell or in the periplasmic space.

The term "variant" according to the invention refers, in particular, to mutants, splice variants, conformation variants, isoforms, allelic variants, species variants and homologues, in particular those, which occur naturally. An allelic variant relates to an alteration in the normal sequence of a gene, the significance of which is often unclear. Complete gene sequencing often identifies numerous allelic variants for a given gene. A homologue is a nucleic acid or amino acid sequence with a different species (or strain) of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise N- and/or C-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein, for example at the N- and/or C-terminus.

In one embodiment, the immunogenic variant lacks the N-terminal secretion sequence.

Amino acid substitution variants are characterized by at least one residue in the sequence being removed and another residue being inserted in its place. In one embodiment, the amino acid substitution variant comprises the substitution of up to 10, 9, 8, 7, 6, 5, 4, 3 or 2 amino acids. Preference is given to modifications being in positions in the amino acid sequence which are not conserved between homologous proteins or peptides and/or to replacing amino acids with other ones having similar properties. Preferably, amino acid substitutions in protein variants are conservative amino acid substitutions. A conservative amino acid substitution involves substitution of an amino acid with another one of the same family of amino acids, i.e., amino acids which are related in their side chains (e.g., in terms of the electrical charge and/or size). Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. However, it is also possible to replace amino acids with other ones having different properties, e.g., substituting one or more (surface-exposed) hydrophobic amino acids with one or more hydrophilic amino acids in order to reduce or inhibit aggregation of the isolated (poly-)peptides, wherein, preferably, other properties of these (poly-)peptides, e.g., their immunogenicity, are not compromised by such amino acid substitutions.

The proteins with the amino acid sequences of SEQ ID NOs: 1 to 7 are proteins from *H. pylori* strain J99 (ATCC700824). Their designations and accession numbers are given in Table 1.

In one embodiment, the immunogenic variant is an equivalent protein from another *H. pylori* strain. In one embodiment, the equivalent protein is a homologue, preferably an orthologue.

An "orthologue" is a homologous gene/protein that is related through speciation from a single ancestral gene/protein, not through gene duplication.

Preferably the degree of similarity, preferably identity, between a given reference amino acid sequence (e.g., an amino acid sequence selected from the group consisting of SEQ ID NOs: 1 to 7, which, optionally, lacks the N-terminal secretion sequence) and an amino acid sequence which is a variant of said given amino acid sequence will be at least about 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree/percentage of similarity or identity is given for the entire length of the reference amino acid sequence. The alignment for determining sequence similarity, preferably sequence identity, can be done with art known tools, preferably using the best sequence alignment, for example, using Align, using standard settings, preferably EMBOSS: needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

In one embodiment, the immunogenic variant comprises an amino acid sequence which is at least 60%, at least 70%, at least 80%, at least 90%, at least 95% or at least 97% (e.g., 97% or 98% or 99%) identical to an amino acid sequence selected from the group consisting of SEQ ID NOs: 1 to 7, i.e., the immunogenic variant comprises an amino acid sequence which is at least 60%, at least 70%, at least 80%, at least 90%, at least 95% or at least 97% (e.g., 97% or 98% or 99%) identical to SEQ ID NO: 1; or the immunogenic variant comprises an amino acid sequence which is at least 60%, at least 70%, at least 80%, at least 90%, at least 95% or at least 97% (e.g., 97% or 98% or 99%) identical to SEQ ID NO: 2; or the immunogenic variant comprises an amino acid sequence which is at least 60%, at least 70%, at least 80%, at least 90%, at least 95% or at least 97% (e.g., 97% or 98% or 99%) identical to SEQ ID NO: 3; or the immunogenic variant comprises an amino acid sequence which is at least 60%, at least 70%, at least 80%, at least 90%, at least 95% or at least 97% (e.g., 97% or 98% or 99%) identical to SEQ ID NO: 4; or
the immunogenic variant comprises an amino acid sequence which is at least 60%, at least 70%, at least 80%, at least 90%, at least 95% or at least 97% (e.g., 97% or 98% or 99%) identical to SEQ ID NO: 5; or
the immunogenic variant comprises an amino acid sequence which is at least 60%, at least 70%, at least 80%, at least 90%, at least 95% or at least 97% (e.g., 97% or 98% or 99%) identical to SEQ ID NO: 6; or
the immunogenic variant comprises an amino acid sequence which is at least 60%, at least 70%, at least 80%, at least 90%, at least 95% or at least 97% (e.g., 97% or 98% or 99%) identical to SEQ ID NO: 7.

In one embodiment, the immunogenic composition further comprises at least one additional antigen from *H. pylori*.

The term "additional antigen from *H. pylori*", as used herein, preferably refers to an antigen which is different from the agents, i.e. the isolated (poly-)peptides and nucleic acid molecules, in accordance with above items (a) and (b).

In a preferred embodiment, the additional antigen is selected from the group consisting of outer membrane proteins and virulence factor proteins of *H. pylori*, immunogenic fragments thereof and nucleic acid molecules encoding these proteins or fragments.

The term "outer membrane protein" refers to proteins that are associated with the outer membrane of *H. pylori*, which includes integral membrane proteins as well as lipoproteins that are anchored to the membrane by means of N-terminally attached lipids. Their structure and function is further described, e.g., in Koebnik et al., 2000. Particularly preferred outer membrane proteins of *H. pylori* for use in accordance with the present invention are selected from the group consisting of BabA, HpaA, Omp18, Omp22 and SabA.

The term "virulence factor protein", as used herein, refers to proteins, e.g., functional proteins, such as enzymes, that contribute to the pathogenicity of *H. pylori* (see, for example, Kalali et al., 2014). A particularly preferred virulence factor protein in accordance with the present invention is gamma-glutamyltranspeptidase (gGT) of *H. pylori* (also referred to as HPGGT or HPG). Suitable HPG proteins are, for example, those described in WO 2008/046650 A1 and include an enzymatically inactivated form of HPG (S451/452A), optionally lacking the N-terminal secretion sequence.

Additional antigens that may be part of the immunogenic composition in accordance with the present invention are also those described in US 2007/0042448 A1 or WO 2004/094467 A2.

In one embodiment, the isolated (poly-)peptide is a fusion protein.

The term "fusion protein" refers to proteins created by joining two or more distinct (poly-) peptides or proteins, preferably head-to-tail (i.e., N-terminus to C-terminus or vice versa), resulting in a single protein with functional properties derived from each of the original proteins.

In one embodiment, the fusion protein comprises
(i) a first amino acid sequence selected from the group consisting of SEQ ID NOs: 1 to 7 or an immunogenic variant thereof or an immunogenic fragment of any of the foregoing and a second, preferably different, amino acid sequence selected from the group consisting of SEQ ID NOs: 1 to 7 or an immunogenic variant thereof or an immunogenic fragment of any of the foregoing; or
(ii) an amino acid sequence selected from the group consisting of SEQ ID NOs: 1 to 7 or an immunogenic variant thereof or an immunogenic fragment of any of the foregoing and at least one additional antigen from *H. pylori*, wherein, preferably, the additional antigen is selected from the group consisting of outer membrane proteins and virulence factor proteins of *H. pylori* and immunogenic fragments thereof; or
(iii) a first amino acid sequence selected from the group consisting of SEQ ID NOs: 1 to 7 or an immunogenic variant thereof or an immunogenic fragment of any of the foregoing, a second, preferably different, amino acid sequence selected from the group consisting of SEQ ID NOs: 1 to 7 or an immunogenic variant thereof or an immunogenic fragment of any of the foregoing, and at least one additional antigen from *H. pylori*, wherein, preferably, the additional antigen is selected from the group consisting of outer membrane proteins and virulence factor proteins of *H. pylori* and immunogenic fragments thereof.

For example, in above alternatives (i) and (iii),
the first amino acid sequence may be SEQ ID NO: 1, and the second amino acid may be selected from the group consisting of SEQ ID NOs: 2 to 7; or
the first amino acid sequence may be SEQ ID NO: 2, and the second amino acid may be selected from the group consisting of SEQ ID NOs: 1 and 3 to 7; or
the first amino acid sequence may be SEQ ID NO: 3, and the second amino acid may be selected from the group consisting of SEQ ID NOs: 1, 2 and 4 to 7; or
the first amino acid sequence may be SEQ ID NO: 4, and the second amino acid may be selected from the group consisting of SEQ ID NOs: 1 to 3 and 5 to 7; or
the first amino acid sequence may be SEQ ID NO: 5, and the second amino acid may be selected from the group consisting of SEQ ID NOs: 1 to 4 and 6 to 7; or
the first amino acid sequence may be SEQ ID NO: 6, and the second amino acid may be selected from the group consisting of SEQ ID NOs: 1 to 5 and 7; or
the first amino acid sequence may be SEQ ID NO: 7, and the second amino acid may be selected from the group consisting of SEQ ID NOs: 1 to 6.

In one embodiment, the fusion protein comprises (i) at least one amino acid sequence selected from the group consisting of SEQ ID NOs: 1 to 7 or an immunogenic variant thereof or an immunogenic fragment of any of the foregoing and (ii) an amino acid sequence allowing the targeted delivery of the fusion protein to a given cell, tissue or organ, preferably an amino acid sequence that targets the fusion protein to a particular cell type, e.g., dendritic cells, as described herein.

The present invention also provides a fusion protein as defined herein.

In one embodiment, the immunogenic composition comprises at least two different isolated (poly-)peptides according to item (a) or at least two different nucleic acid molecules according to item (b).

A nucleic acid molecule may according to the invention be in the form of a molecule, which is single-stranded or double-stranded and linear or covalently closed to form a circle. In one embodiment, the nucleic acid molecule is DNA or RNA.

In the context of the present invention, the term "DNA" relates to a molecule, which comprises deoxyribonucleotide residues and preferably is entirely or substantially composed of deoxyribonucleotide residues. "Deoxyribonucleotide" relates to a nucleotide, which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA, which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally occurring DNA.

In the context of the present invention, the term "RNA" relates to a molecule, which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA, which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally occurring RNA. According to the invention, "RNA" refers to single-stranded RNA or double stranded RNA. In one embodiment, the RNA is mRNA. In one embodiment, the RNA is in vitro transcribed RNA (IVT RNA) or synthetic RNA.

Also encompassed by the present invention are nucleic acid molecules, which hybridize under stringent hybridization conditions to a nucleic acid molecule according to above item (b).

"Stringent hybridization conditions", as defined herein, involve hybridizing at 68° C. in 5×SSC/5×Denhardt's solution/1.0% SDS, and washing in 0.2×SSC/0.1% SDS at room temperature, or involve an art-recognized equivalent thereof (e.g., conditions in which a hybridization is carried out at 60° C. in 2.5×SSC buffer, followed by several washing steps at 37° C. in a low buffer concentration, and remains stable). The parameters of salt concentration and temperature can be varied to achieve the optimal level of identity between the oligonucleotides and the target nucleic acid. Guidance regarding such conditions is available in the art, for example, by Molecular Cloning: A Laboratory Manual, $3^{rd}$ Edition, J. Sambrook et al. eds., Cold Spring Harbor Laboratory Press, Cold Spring Harbor 2000, and Ausubel et al. (eds.), 1995, Current Protocols in Molecular Biology, (John Wiley and Sons, N.Y.) at Unit 2.10.

In one embodiment, the nucleic acid molecule is codon-optimized, e.g., for expression in bacteria other than *H. pylori*, such as *E. coli*, or for expression in eukaryotic cells, such as mammalian cells (e.g., CHO cells, BHK cells, COS cells and HEK293 cells) or insect cells (e.g., SF9 cells, SF21 cells and High Five™ cells).

In one embodiment, the nucleic acid molecule is contained/comprised in a vector.

The term "vector", as used herein, includes any vectors known to the skilled person, including plasmid vectors, cosmid vectors, phage vectors, such as lambda phage, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In one embodiment, the immunogenic composition further comprises at least one adjuvant.

The term "adjuvant" refers to a substance which enhances the immune response to an antigen, e.g., to an agent in accordance with above items (a) and (b) or an additional antigen from *H. pylori* as defined herein, for example by providing a general stimulation of the immune system. Suitable adjuvants are known to a person skilled in the art and include toxin-based adjuvants, TLR ligand-based adjuvants, nucleic acid/vector-based adjuvants, protein-based adjuvants, polymer-based adjuvants, mucosal adjuvants, ISCOM matrices and combinations of any of the foregoing. Particular adjuvants include, but are not limited to, polycationic polymers/peptides, immunostimulatory deoxynucleotides (ODNs), synthetic KLK peptides, neuroactive compounds (e.g., human growth hormone), alumn, Freund's complete or incomplete adjuvants, cholera toxin (CT), CTA1-DD, heat-labile enterotoxin (LT), mutants of CT or LT, poly-IC, dendritic cell (DC) binding peptides and C3d fusion protein. In one embodiment, the TLR ligand-based adjuvant is a TLR5 ligand, e.g., from the group of bacterial flagellins, such as those described in WO 2010/050903 A1, Mori et al., 2012 and Song et al., 2015. In one embodiment, the adjuvant is selected from the group consisting of cholera toxin (CT), CTA1-DD and heat-labile enterotoxin (LT).

According to the invention, the immunogenic composition contains an effective amount of the active agents, i.e., the (poly-)peptides or nucleic acid molecules described herein, to generate the desired reaction or the desired effect.

An immunogenic composition in accordance with the present invention is preferably sterile. Immunogenic compositions can be provided in a uniform dosage form and may be prepared in a manner known per se. An immunogenic composition in accordance with the present invention may, e.g., be in the form of a solution or suspension.

The immunogenic composition may further comprise one or more carriers and/or excipients, all of which are preferably pharmaceutically acceptable. The term "pharmaceutically acceptable", as used herein, refers to the non-toxicity of a material, which, preferably, does not interact with the action of the active agent of the immunogenic composition.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a subject.

Possible carrier substances (e.g., diluents) for parenteral administration are, for example, sterile water, Ringer's solution, Lactated Ringer's solution, physiological saline, bacteriostatic saline (e.g., saline containing 0.9% benzyl alcohol), phosphate-buffered saline (PBS), Hank's solution, fixed oils, polyalkylene glycols, hydrogenated naphthalenes and biocompatible lactide polymers, lactide/glycolide copolymers or polyoxyethylene/polyoxy-propylene copolymers.

The resulting solutions or suspensions are preferably isotonic to the blood of the recipient.

The term "excipient", as used herein, is intended to include all substances which may be present in a pharmaceutical composition, such as an immunogenic composition in accordance with the present invention, and which are not active ingredients, such as salts, binders (e.g., lactose, dextrose, sucrose, trehalose, sorbitol, mannitol), lubricants, thickeners, surface active agents, preservatives, emulsifiers, buffer substances, stabilizing agents, flavouring agents, or colorants.

Salts, which are not pharmaceutically acceptable, may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts. Salts may be added to adjust the ionic strength or tonicity.

Suitable preservatives for use in a pharmaceutical composition include antioxidants, citric acid, sodium citrate, benzalkonium chloride, chlorobutanol, cysteine, methionine, parabens and thimerosal.

Suitable buffer substances for use in a pharmaceutical composition include acetic acid in a salt, citric acid in a salt, boric acid in a salt and phosphoric acid in a salt. Other suitable buffer substances include arginine-hydrochloride and arginine-phosphate.

Suitable stabilizing agents include glycerol, ascorbate and histidine.

The immunogenic compositions according to the present invention may also be formulated as described in U.S. Pat. No. 6,838,089 B1 and U.S. Pat. No. 6,372,260 B1.

The immunogenic composition in accordance with the present invention may also be formulated as a stable lyophilized product that is reconstituted with an appropriate diluent, which, optionally, comprises one or more excipients as described above.

In one embodiment, the immunogenic composition is a vaccine or is comprised in a vaccine.

The term "vaccine" refers to a preparation that confers or improves immunity to a particular disease. A vaccine in accordance with the present invention confers or improves immunity to a disease or disorder caused by or associated with *H. pylori*, in particular the specific diseases mentioned herein.

The present invention further provides an immunogenic composition as defined herein for use as a medicament.

The term "medicament", as used herein, refers to a substance/composition used in therapy, i.e., in the prevention or treatment of a disease or disorder. According to the invention, the terms "disease" or "disorder" refer to any pathological state.

In yet another aspect the present invention relates to an immunogenic composition as defined herein or to a polypeptide ligand specifically binding to an isolated (poly-)peptide according to item (a) for use in a method of preventing or treating a disease or disorder caused by or associated with *H. pylori*, wherein, preferably, the disease or disorder is selected from the group consisting of *H. pylori* infection and gastroduodenal disorders caused by *H. pylori*.

In a further aspect, the present invention relates to the use of an immunogenic composition as defined herein or of a polypeptide ligand specifically binding to an isolated (poly-)peptide according to item (a) in the manufacture of a medicament for preventing or treating a disease or disorder caused by or associated with *H. pylori*, wherein, preferably, the disease or disorder is selected from the group consisting of *H. pylori* infection and gastroduodenal disorders caused by *H. pylori*.

In another aspect, the present invention relates to a method of preventing or treating a disease or disorder caused by or associated with *H. pylori*, wherein, preferably, the disease or disorder is selected from the group consisting of *H. pylori* infection and gastroduodenal disorders caused by *H. pylori*, the method comprising administering an immunogenic composition as defined herein or a polypeptide ligand specifically binding to an isolated (poly-)peptide according to item (a) to a subject in need thereof.

The term "treating", as used herein, relates to any treatment, which improves the health status and/or prolongs (increases) the lifespan of a patient.

The term "infection", as used herein, refers to the invasion of a subject's body tissues by disease-causing agents (here: *H. pylori*), their multiplication, and the reaction of the tissues to these agents and the toxins they produce.

The term "gastroduodenal disorder" (or simply "stomach disorder"), as used herein, refers to a disorder affecting the stomach and the adjoining duodenum. "Gastroduodenal disorders caused by *H. pylori*" are known to a person skilled in the art and include, for example, gastritis, chronic gastritis, gastric atrophy, gastric or duodenal ulcer, stomach cancer (also referred to as gastric cancer) and MALT lymphoma.

In one embodiment, the polypeptide ligand is selected from the group consisting of an antibody, an antibody derivative and an antibody mimetic.

The term "antibody" (also referred to as immunoglobulin, Ig) refers to a glycoprotein comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody derivative", as used herein, refers to a molecule comprising at least one antibody variable domain, but not having the overall structure of an antibody such as IgA, IgD, IgE, IgG, IgM, IgY or IgW, although still being capable of binding a target molecule. Said derivatives may be, but are not limited to functional (i.e. target binding, particularly specifically target binding) antibody fragments, such as Fab, Fab2, scFv, Fv, or parts thereof, or other derivatives or combinations of the immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is monovalent. More preferably, the derivative is a single chain antibody, most preferably having the structure VL-peptide linker-VH or VH-peptide linker-VL.

The term "antibody mimetic", as used herein, refers to artificial (poly-)peptides that, like antibodies, can specifically bind antigens, but that are not structurally related to antibodies. They are usually significantly smaller than antibodies with a molar mass of about 3 to 20 kDa. Non-limiting examples of antibody mimetics are affibodies, affilins, affimers, affitins, anticalins, avimers, DARPins, fynomers, Kunits domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the $10^{th}$ type III domain of fibronectin, or synthetic peptide ligands, e.g., from a (random) peptide library. Synthetic peptide ligands have non-naturally occurring amino acid sequences that function to bind a particular target molecule.

The terms "specific binding" or "specifically binding", as used herein, mean that a binding to a target, such as an epitope for which a binding agent, such as a polypeptide ligand (e.g., an antibody), is specific, is stronger by comparison with the binding to another target. A "stronger binding" can be characterized for example by a lower dissociation constant ($K_D$). In one embodiment, a binding agent is specific for a predetermined target if it is capable of binding to said predetermined target while it is not capable of binding to other targets. In one embodiment, a binding agent that "specifically binds" a target has an $K_D$ value of less than $10^{-5}$ M (e.g., $10^{-6}$, $10^{-7}$, $10^{-8}$, $10^{-9}$, $10^{-10}$, $10^{-11}$, and $10^{-12}$ or less) for that target. The $K_D$ value of a given binding agent is influenced both by the on and off-rate of the binding agent and varies with the temperature. It is preferred in the context of the present invention that the $K_D$ value is below above indicated values at room temperature. The binding conditions are preferably physiological conditions. The skilled person is aware of various assays to determine the $K_D$ value. A preferred assay system is a competition assay.

The agents and compositions described herein may be administered via any conventional route, such as by enteral administration or by parenteral administration including by injection or infusion. In one embodiment, administration is parenterally, e.g., intradermally, subcutaneously or intramuscularly. In one embodiment, mucosal administration is used, e.g., orally or sublingually.

The agents and compositions described herein are administered in effective amounts. An "effective amount" refers to the amount, which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent or composition described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a subject is insufficient with an initial dose, higher doses (or effectively higher doses achieved by a different, more localized route of administration) may be used.

The present invention further provides a kit comprising an immunogenic composition as defined herein.

As used herein, the term "kit of parts (in short: kit)" refers to an article of manufacture comprising one or more containers and, optionally, a data carrier. Said one or more containers may be filled with one or more of the means or reagents disclosed herein. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the kit in accordance with the present invention.

The present invention further provides a method of detecting *H. pylori* infection in a subject, comprising the steps of:
(a) providing at least one isolated (poly-)peptide as defined herein, wherein, preferably, the at least one isolated (poly-)peptide is immobilized on a solid support;
(b) contacting the at least one isolated (poly-)peptide with a biological sample obtained from the subject; and
(c) determining the presence or absence of antibodies specifically binding to the at least one isolated (poly-)peptide in the biological sample,
wherein the presence of antibodies indicates *H. pylori* infection in the subject.

In one embodiment, the method comprises the use of at least one additional antigen from *H. pylori*, wherein, preferably, the at least one additional antigen is immobilized on a solid support.

In one embodiment, a plurality of different isolated (poly-)peptides as defined herein is used in the above method, e.g., in the form of a panel comprising the plurality of different isolated (poly-) peptides as defined herein. In one embodiment, the panel further comprises at least one additional antigen from *H. pylori*.

In such embodiments, *H. pylori* infection in the subject is preferably indicated by the presence of antibodies specifically binding to at least one of the plurality of different isolated (poly-)peptides as defined herein.

The term "solid support" (also referred to as solid phase), as used herein, preferably refers to any solid support able to bind to an isolated (poly-)peptide as defined herein. Such supports may comprise support materials such as glass, polystyrene, polypropylene, polyethylene, dextran, nylon, natural or modified celluloses (e.g., nitrocellulose), polyacrylamides, agaroses and magnetite. The support may have any possible structural configuration as long as the molecule bound thereto, such as an isolated (poly-)peptide as defined herein, is able to bind to its respective binding partner. Suitable configurations include a spherical configuration (e.g., beads), a cylindrical configuration such as the inside and/or bottom of a test vessel or well (which may be part of a multi-well plate, such as an ELISA plate), or a flat configuration such as test strips (e.g., a nitrocellulose strip) etc.

According to the present invention, a "biological sample" may be a tissue sample, including body fluids, and/or a cellular sample and can be obtained in a conventional way, such as by tissue biopsy, including punch biopsy, and removal of blood, bronchial aspirate, sputum, urine, feces or other body fluids. The term "biological sample" also includes according to the invention fractions of biological samples. Particularly preferred biological samples in accordance with the present invention are body fluids, such as blood serum and blood plasma.

Possibilities for carrying out the step of "determining the presence or absence of antibodies specifically binding to the at least one isolated (poly-)peptide in the biological sample" are known to the person skilled in the art.

It is preferred according to the invention for antibodies to be detected in an immunoassay, preferably in a solid-phase immunoassay, with direct or indirect coupling of a binding partner. The detection can take place in an ELISA, a radioimmunoassay (RIA) or a fluorescence or chemiluminescence immunoassay. The procedure for these detection methods is known to the person skilled in the art. In one embodiment, the antibodies are detected by using a binding partner which is an anti-human immunoglobulin antibody comprising a detectable label as defined herein.

It is also possible according to the invention to detect antibodies in an agglutination test or gel diffusion test. These detection methods are also known to the person skilled in the art.

In one embodiment, the method comprises, after step (b) and prior to step (c), a step of removing unbound antibodies (=wash step).

The present invention further provides the use of a (poly-)peptide comprising (i) an amino acid sequence selected from the group consisting of SEQ ID NOs: 1 to 7; or (ii) an immunogenic variant of (i); or (iii) an immunogenic fragment of (i) or (ii), or of an antibody specifically binding to the (poly-)peptide or fragment or variant thereof as a biomarker for H. pylori infection.

The term "biomarker", as used herein, refers to a distinctive biological or biologically derived indicator of a process, event or condition.

The present invention further provides a kit comprising at least one isolated (poly-)peptide as defined herein, preferably a plurality of different isolated (poly-)peptides as defined herein.

In one embodiment, the at least one isolated (poly-)peptide as defined herein or the plurality of different isolated (poly-)peptides as defined herein is/are immobilized on a solid support.

In one embodiment, the kit comprises at least one additional antigen from H. pylori.

The present invention further provides the use of a kit as defined above for detecting H. pylori infection in a subject.

The present invention is further illustrated by the following examples, which are not to be construed as limiting the scope of the invention.

EXAMPLES

Example 1: Identification of Novel H. pylori Vaccine Candidates by Surfome Shaving In surfome shaving, a live bacterial culture is treated with trypsin and compared with a culture without treatment. By treating the culture with trypsin and/or Proteinase K, the protease shaves all proteins from the bacterial surface, which are exposed and accessible. The derived peptides are then analyzed by mass spectrometry and the individual proteins are identified (Rodriguez-Ortega et al., 2006). Protein intensities are quantified proteome-wide using quantitative mass spectrometry (Cox and Mann, 2008), enabling direct comparison of the samples by identifying proteins with different abundances. The list of proteins obtained is narrowed down using rational criteria for pan-protective vaccine candidates, ideally being conserved greater than 90% within the same species (Moffit et al., 2011). The resulting proteins are then recombinantly produced in E. coli and tested for their protective properties in in vivo vaccine studies (see FIG. 1).

Using the above approach, the inventors analyzed the surfome of H. pylori and identified seven novel vaccine candidates that are more than 90% sequence identical within the same species and/or are believed to play a role in pathogenesis, which are listed in below Table 1.

TABLE 1

List of vaccine candidates as identified herein, including accession numbers and assigned SEQ ID NOs. The protein trxA served as reference for identity within the UniProt Reference Cluster. At the time of access (August 2014), 265 strains of H. pylori were annotated in UniProt.

| Protein | Strain | UniProt Reference Cluster 90% sequence identity | UniProt ID | NCBI locus tag | SEQ ID NOs |
|---------|--------|---|---|---|---|
| jhp_0775 | J99 | 278 | Q9ZL07 | JHP_RS04025 | 1, 8 |
| jhp_0119 | J99 | 300 | Q9ZMU8 | JHP_RS00650 | 2, 9 |
| jhp_0173 | J99 | 57 | Q9ZMP5 | JHP_RS00925 | 3, 10 |
| jhp_1381 | J99 | 281 | Q9ZJD1 | JHP_RS07235 | 4, 11 |
| jhp_0552 | J99 | 336 | Q9ZLM7 | JHP_RS02885 | 5, 12 |
| jhp_0305 | J99 | 18 | Q9ZMB6 | JHP_RS01600 | 6, 13 |
| clpP | J99 | 267 | Q9ZL50 | JHP_RS03795 | 7, 14 |
| trxA (reference) | J99 | 262 | P66929 | — | — |

Figure 2:
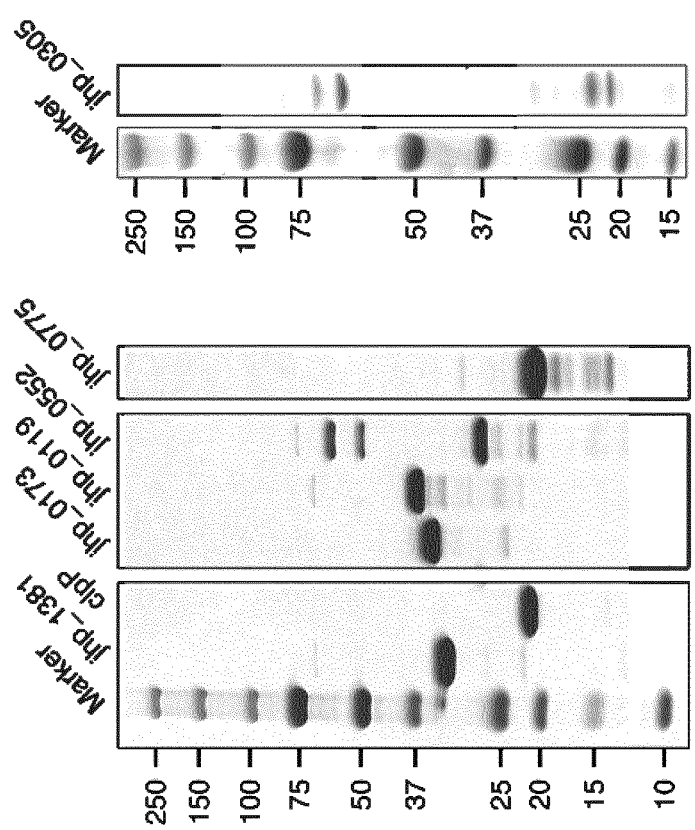
FIG. 2 shows a Coomassie-stained SDS-gel of newly identified vaccine candidates purified by Ni-NTA affinity chromatography and size exclusion chromatography.

The protein constructs listed in Table 2 (which include truncated versions of the vaccine candidates lacking the predicted N-terminal signal sequence; see SEQ ID NOs: 15 to 19) were recombinantly expressed in E. coli BL21 (DE3) cells, subsequently purified by Ni-NTA affinity chromatography and size exclusion chromatography, and stored at −80° C. in an isotonic and isohydric buffer. FIG. 2 shows a Coomassie-stained SDS-gel of the purified proteins.

TABLE 2

List of protein constructs used for immunization studies.

| Construct | Sequence of vaccine candidate | Tag(s) | SEQ ID NOs |
|---|---|---|---|
| jhp_0775 | Amino acids 34-201 of jhp_0775 of strain J99 | C-terminal 6x His-tag | 15, 22 |
| jhp_0119 | Amino acids 23-285 of jhp_0119 of strain J99 | C-terminal 6x His-tag | 16, 23 |
| jhp_0173 | Amino acids 44-268 of jhp_0173 of strain J99 | C-terminal 6x His-tag | 17, 24 |
| jhp_1381 | Amino acids 32-329 of jhp_1381 of strain J99 | C-terminal 6x His-tag | 18, 25 |
| jhp_0552 | Amino acids 21-477 of jhp_0552 of strain J99 | C-terminal 6x His-tag | 19, 26 |
| jhp_0305 | Full-length jhp_305 of strain J99 | C-terminal 6x His-tag | 20, 27 |
| clpP | Full-length clpP of strain J99 | C-terminal 6x His-tag | 21, 28 |

Figure 3:
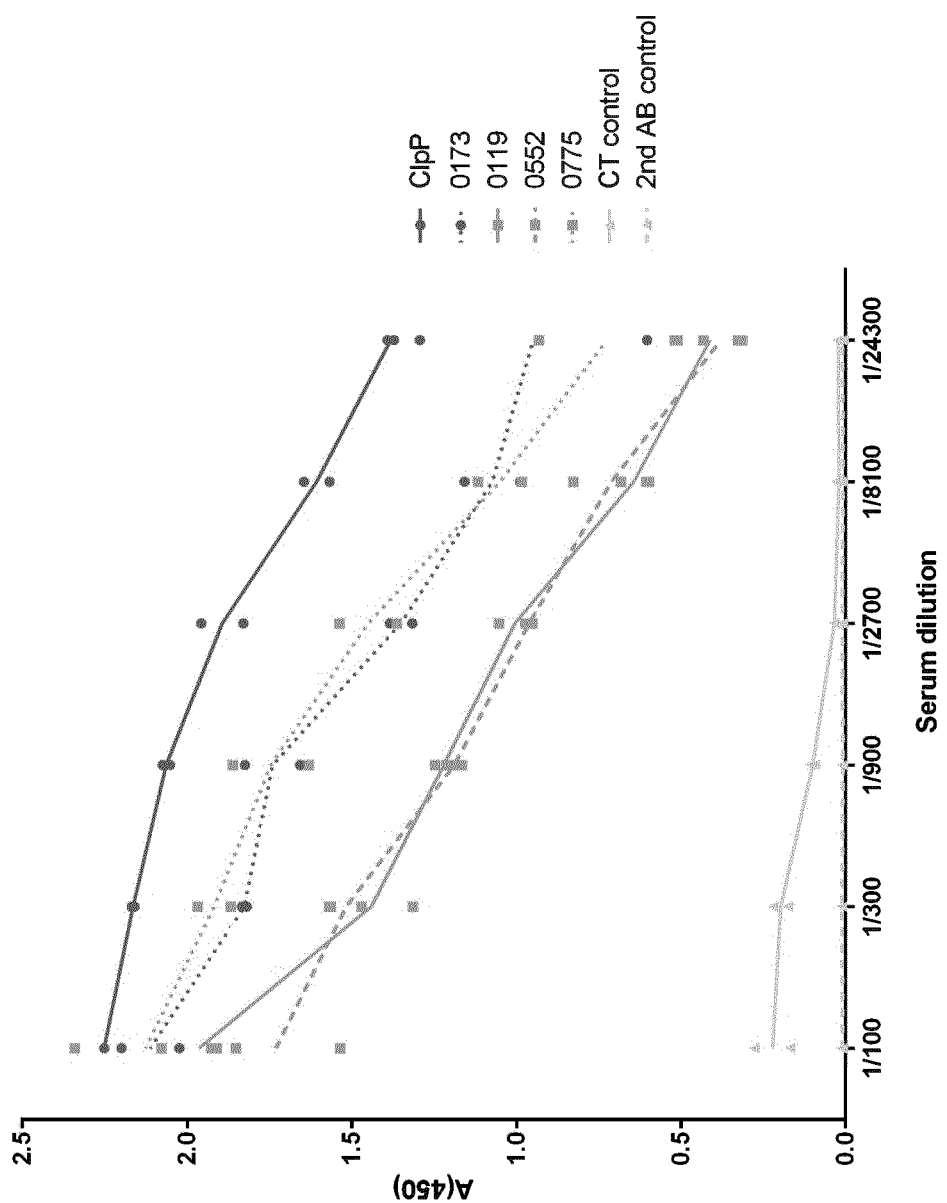
FIG. 3 shows enzyme-linked immunosorbent assay (ELISA) data for newly identified vaccine candidates indicating that each of the tested vaccine candidates is able to elicit a humoral immune response.

For immunization studies in naïve mice, 30 μg of each protein were administered intraperitoneally four times on days 0, 7, 14 and 21 together with 10 µg cholera toxin (CT) as a mucosal adjuvant. ELISA plates were coated with the corresponding protein and incubated with the anti-serum obtained from the mice. Serum antibodies binding to the adsorbed proteins were detected by a secondary anti mouse antibody-conjugate. All antisera showed a response, whereas the CT control and $2^{nd}$ antibody control did not (FIG. 3). The ELISA showed that all tested proteins were able to elicit a humoral immune response after immunization with CT as adjuvant, i.e., all tested vaccine candidates proved to be immunogenic.

Figure 4:
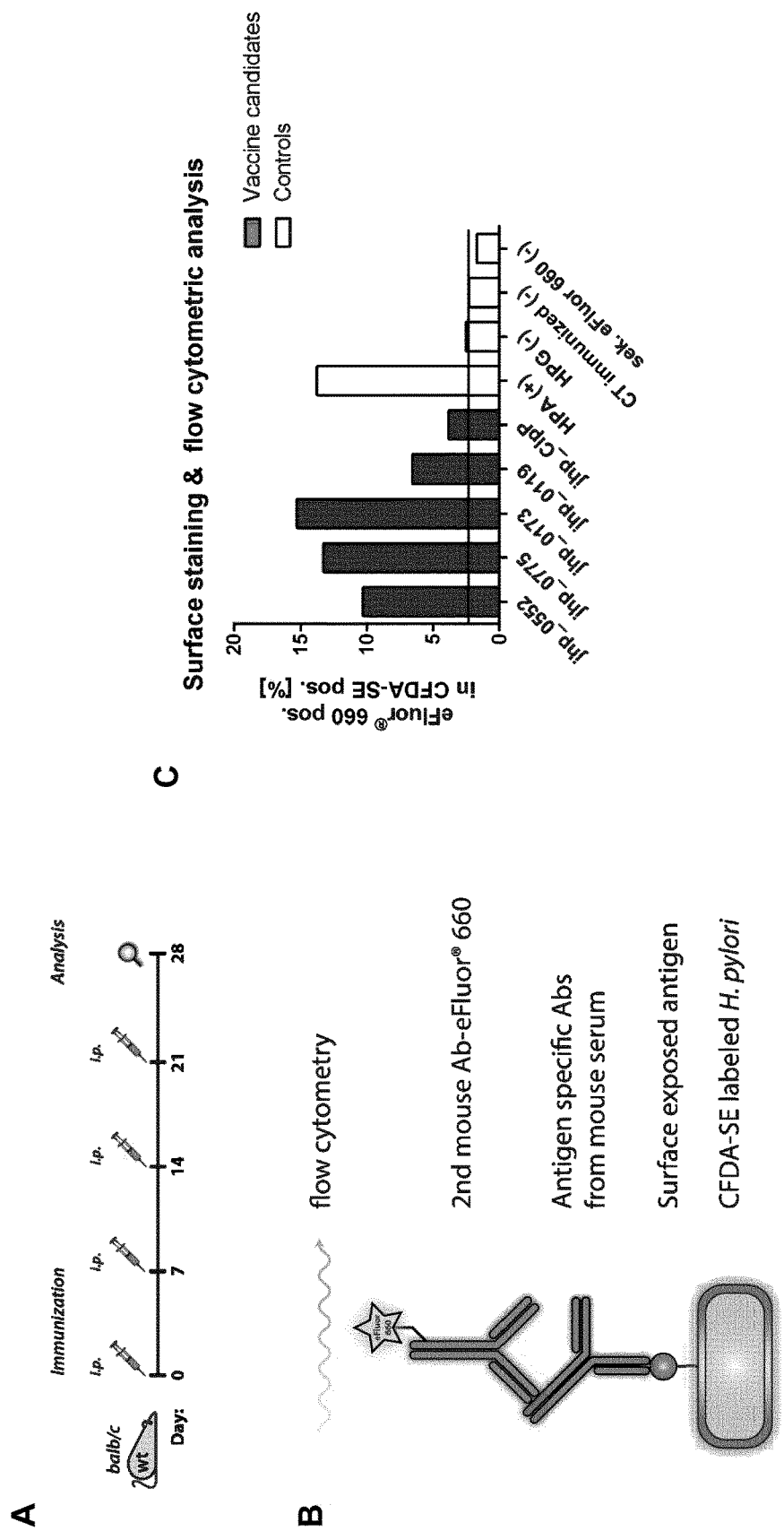
FIG. 4 shows a flow cytometric analysis confirming that each of the tested vaccine candidates is exposed to the cell surface, see (B) and (C). Specific antibodies against the vaccine candidates and control proteins were raised by immunization of balb/c mice (A).

To confirm surface exposure of the vaccine candidates, the surface of *H. pylori* J99 was stained with specific antibodies recognizing the respective proteins. Antiserum was raised against the candidates by immunizing wild-type balb/c mice intraperitoneally (i.p.) with 30 µg antigen and 10 µg CT as adjuvant four times at an interval of one week (FIG. 4 A). Subsequently, the corresponding serum was prepared from whole blood, further purified by Protein A affinity chromatography, and the concentration of the isolated antibodies was adjusted to approximately 1 mg/ml. *H. pylori* J99 was CFDA-SE labeled and incubated with the antibodies. The antibody-antigen interaction was detected by labeling with a secondary mouse eFluor® 660 antibody with subsequent flow cytometric analysis (FIG. 4 B). The experiment was controlled by antibodies derived from immunizing with HpaA (HPA; UniProt ID B5Z7F9), a well-known outer membrane protein of *H. pylori*, HPG (UniProt ID O25743), a protein located in the cytoplasm and inside of outer membrane vesicles, and only CT without antigen ("CT immunized").

Staining with the candidate-specific antibodies showed an increase in fluorescence intensity well above the CT immunized cutoff control for all tested vaccine candidates, confirming their surface exposure (FIG. 4 C). The HPA and HPG controls showed a significant increase or almost no increase in fluorescence intensity, respectively, thereby validating the experimental setup.

Example 2: In Vivo Efficacy of Jhp_0775

Figure 5:
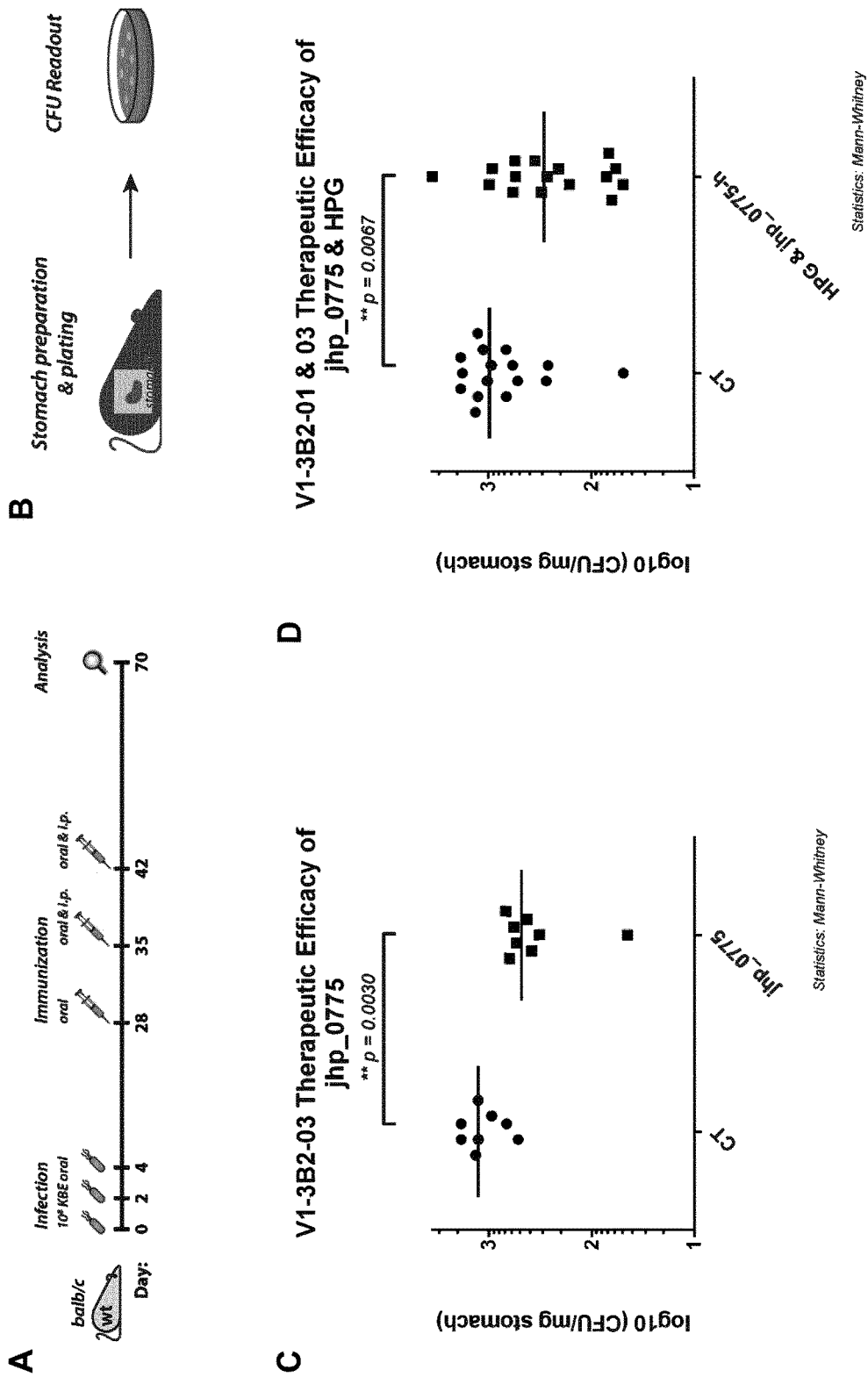
FIG. 5 shows vaccination studies in mice confirming that immunization with jhp_0775 alone (C) and in combination with *H. pylori* gamma-glutamyltranspeptidase (HPG) (D) results in a significant reduction in bacterial load. The experimental set-up is shown in (A) and (B).

To test the therapeutic efficacy of jhp_0775, mice were vaccinated in a therapeutic setup. Wild-type balb/c mice were infected orally with $10^8$ *H. pylori* SS1 on day 0, 2 and 4. Subsequently, the animals were immunized orally on day 28 and orally combined with i.p. on day 35 and 42 (FIG. 5 A). For oral immunization with jhp_0775 and jhp_0775 combined with HPG, 100 µg antigen and 30 µg antigen, respectively, were administered with 10 µg CT. For i.p. immunization, 30 µg antigen was administered with 10 µg CT. On day 70, mice were sacrificed, bacteria extracted from the stomach and plated on agar-plates. After 5 days, colony forming units (CFUs) were counted (FIG. 5 B). Data in FIG. 5 C/D are shown as median values, and p-values were determined by a Mann-Whitney U test. Immunization with jhp_0775 alone and in combination with HPG reduced the bacterial load significantly, with a p-value of 0.0030 and 0.0067, respectively. These results confirm the efficacy of jhp_0775 alone and in combination with HPG as a vaccine.

Figure 6:
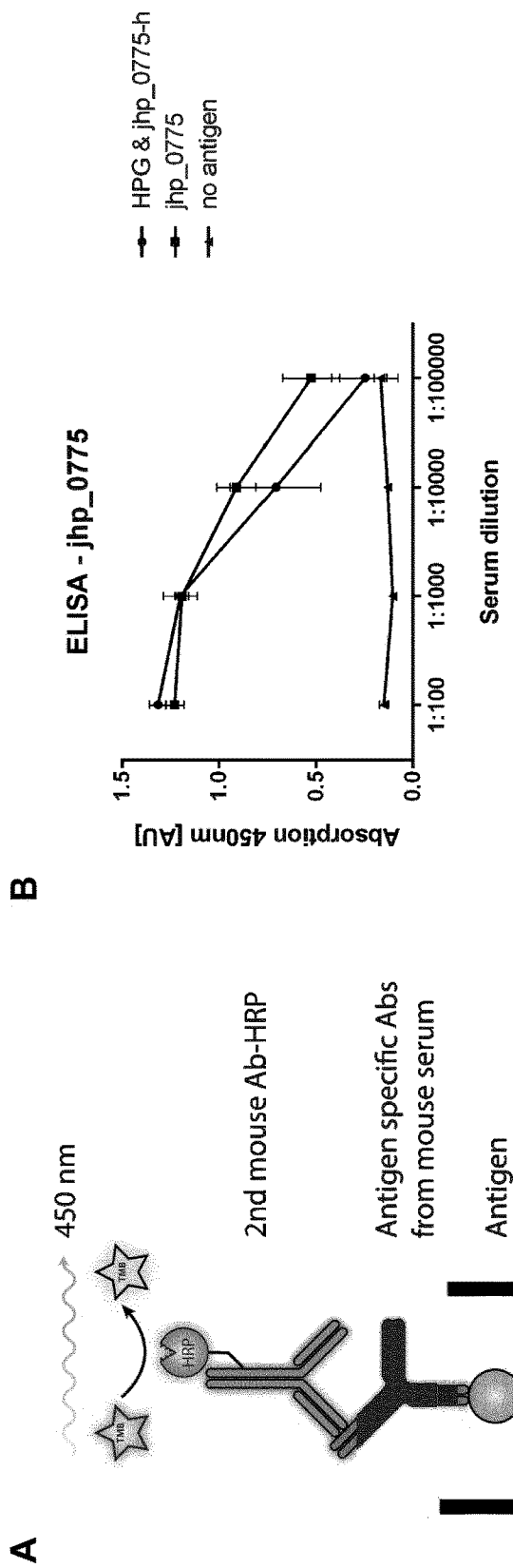
FIG. 6 shows an enzyme-linked immunosorbent assay (ELISA) showing the humoral response in mice upon immunization with jhp_0775 alone and in combination with HPG (B). The mode of detection underlying the assay is shown in (A).

Serum was prepared from whole blood of the same experiment as described above (FIG. 5 A). For analyzing the humoral response by antigen-specific ELISA, antigens were coated onto a 96-well microtiter plate. Subsequently, wells were blocked, and serum was added in a serial dilution ranging from 1:100 to 1:100000. Next, a secondary anti-mouse-IgG-HRP conjugate was added (FIG. 6 A). After incubation, TMB substrate solution was added, and the enzymatic reaction was stopped with 2N $H_2SO_4$. Washing in between incubation steps was carried out four times with PBS/0.05% Tween20. Both groups receiving jhp_0775 showed high absorptions being reduced upon dilution in the anti-jhp_0775 ELISA, while the background remained constant on a low level (FIG. 6 B). These results show the immunogenicity of jhp_0775 upon immunization.

Figure 7:
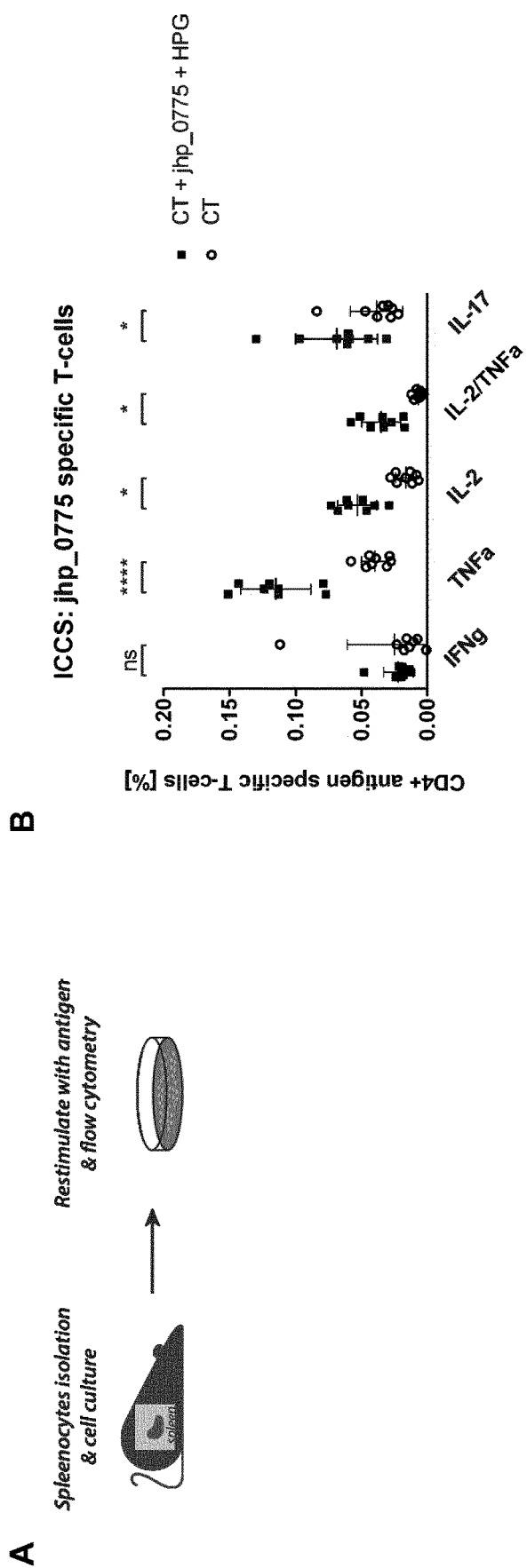
FIG. 7 shows intracellular cytokine staining (ICCS) of spleenocytes indicating that immunization with jhp_0775 induces specific T-cell responses in mice, see (A) and (B).

For analyzing the cellular immune response against jhp_0775 by intracellular cytokine staining (ICCS), spleenocytes were isolated from the same experiment as described above (FIG. 5 A). Subsequently, recombinant antigen was added to the cells and incubated for 2 hours. Next, Golgi-Plug™ was added to suppress cytokine secretion, leading to their intracellular accumulation. Then, cells were stained with EMA (viability) and an antibody-panel against CD4, IFNg, TNFa, IL-2 and IL-17. Subsequently, cells were analyzed by flow cytometry (FIG. 7 A), gating on CD4+ cells and counting at least 100 000 cells. Data are shown as mean values±SD, and p-values were determined by a Šidák multiple comparison test, where asterisks show significant differences between groups (****p<0.0001, *p<0.05). CD4+ cells of the group immunized with jhp_0775 and HPG showed significant production of the cytokines TNFa, IL-2 and IL-17, demonstrating jhp_0775's ability to induce T-cell responses upon immunization of mice.

REFERENCES

1. Apostolopoulos, V. et al., 2013. Targeting antigens to dendritic cell receptors for vaccine development. Journal of Drug Delivery, 2013:869718.
2. Blaser, M. J. et al., 1995. Infection with *Helicobacter pylori* strains possessing cagA is associated with an increased risk of developing adenocarcinoma of the stomach. Cancer research, 55(10), pp. 2111-2115.
3. Cox, J. & Mann, M., 2008. MaxQuant enables high peptide identification rates, individualized p.p.b.-range mass accuracies and proteome-wide protein quantification. Nature Biotechnology, 26(12), pp. 1367-1372.
4. Forman, D., 1996. *Helicobacter pylori* and gastric cancer. Scandinavian journal of gastroenterology. Supplement, 214, pp. 31-3-discussion 40-3.
5. Gao, W. et al., 2010. The evolution of *Helicobacter pylori* antibiotics resistance over 10 years in Beijing, China. Helicobacter, 15(5), pp. 460-466.
6. Graham, D. Y. & Shiotani, A., 2005. The time to eradicate gastric cancer is now. Gut, 54(6), pp. 735-738.
7. Jemal, A. et al., 2011. Global cancer statistics. CA: a cancer journal for clinicians, 61(2), pp. 69-90.
8. Kalali, B. et al., 2014. *H. pylori* virulence factors: influence on immune system and pathology. Mediators of Inflammation, 2014:426309.
9. Koebnik, R. et al., 2000. Structure and function of bacterial outer membrane proteins:
barrels in a nutshell. Molecular Microbiology, 37(2), pp. 239-253.
10. Moffitt, K. L. et al., 2011. TH17-Based Vaccine Design for Prevention of *Streptococcus pneumoniae* Colonization. Cell Host & Microbe, 9(2), pp. 158-165.
11. Mori, J. et al., 2012. Chimeric flagellin as the self-adjucanting antigen for the activation of immune response against *Helicobacter pylori*. Vaccine, 30(40), pp. 5856-5863.
12. Nomura, A. et al., 1994. *Helicobacter pylori* infection and the risk for duodenal and gastric ulceration. Annals of internal medicine, 120(12), pp. 977-981.

13. Parsonnet, J. et al., 1991. *Helicobacter pylori* infection and the risk of gastric carcinoma. New England Journal of Medicine, 325(16), pp. 1127-1131.
14. Perez-Perez, G. I., Rothenbacher, D. & Brenner, H., 2004. Epidemiology of *Helicobacter pylori* infection. *Helicobacter*, 9 Suppl 1, pp. 1-6.
15. Rodriguez-Ortega, M. J: et al., 2006. Characterization and identification of vaccine candidate proteins through analysis of the group A *Streptococcus* surface proteome. Nature Biotechnology, 24(2), pp. 191-197.
16. Shiota, S. et al., 2010. Population-based strategies for *Helicobacter pylori*-associated disease management: a Japanese perspective. Expert review of gastroenterology & hepatology, 4(2), pp. 149-156.
17. Sioud, M. et al., 2013. A novel peptide carrier for efficient targeting of antigens and nucleic acids to dendritic cells. FASEB J., 27(8), pp. 3272-3283.
18. Song, H. et al., 2015. A novel chimeric flagellum fused with the multi-epitope vaccine CTB-UE prevents *Helicobacter pylori*-induced gastric cancer in a BALB/c mouse model. Appl Microbiol Biotechnol., 99(22), pp. 9495-9502.
19. United States Centers for Disease Control and Prevention (2011). "A CDC framework for preventing infectious diseases", accessed Dec. 20, 2012.

The invention claimed is:

1. A method of preventing or treating *H. pylori* infection, the method comprising the step of administering to a subject in need thereof an effective amount of an immunogenic composition comprising at least one isolated (poly-)peptide comprising (i) the amino acid sequence SEQ ID NO: 1 or (ii) an immunogenic fragment of (i), wherein the immunogenic fragment comprises amino acids 34 to 201 of SEQ ID NO: 1, wherein the immunogenic composition further comprises *H. pylori* gamma-glutamyltranspeptidase (HPG) as addition antigen.

2. The method according to claim 1, wherein the isolated (poly-)peptide is a recombinant (poly-)peptide.

3. The method according to claim 1, wherein the immunogenic composition further comprises at least one additional antigen from *H. pylori*.

4. The method according to claim 3, wherein the additional antigen is selected from the group consisting of outer membrane proteins and virulence factor proteins of *H. pylori* and immunogenic fragments thereof.

5. The method according to claim 1, wherein the isolated (poly-) peptide is a fusion protein.

6. The method according to claim 5, wherein the fusion protein comprises amino acid sequence of SEQ ID NO: 1 or an immunogenic fragment thereof, wherein the immunogenic fragment comprises amino acids 34 to 201 of SEQ ID NO: 1, and (ii) *H. pylori* gamma-glutamyltranspeptidase (HPG).

7. The method according to claim 6, wherein the additional antigen is selected from the group consisting of outer membrane proteins and virulence factor proteins of *H. pylori* and immunogenic fragments thereof.

8. The method according to claim 1, wherein the immunogenic composition further comprises at least one different isolated (poly-) peptides comprising (i) an amino acid sequence selected from the group consisting of SEQ ID NOs: 1 to 7; or (ii) an immunogenic variant of (i) comprising an amino acid sequence which is at least 90% identical to an amino acid sequence selected from the group consisting of SEQ ID NOs: 1 to 7; or (iii) an immunogenic fragment of (i) or (ii), wherein the immunogenic fragment comprises at least 6 consecutive amino acids of an amino acid sequence selected from the group consisting of SEQ ID NOs: 1 to 7.

9. The method according to claim 1, wherein the immunogenic composition further comprises at least one adjuvant.

10. The method according to claim 9, wherein the at least one adjuvant is selected from the group consisting of toxin-based adjuvants, toll-like receptor (TLR) ligand-based adjuvants, nucleic acid- or vector-based adjuvants, protein-based adjuvants, polymer-based adjuvants, mucosal adjuvants, immune stimulating complex (ISCOM) matrices and combinations of any of the foregoing.

11. The method according to claim 9, wherein the at least one adjuvant is selected from the group consisting of polycationic polymers or peptides, immunostimulatory deoxynucleotides (ODNs), synthetic KLK peptides, neuroactive compounds, alumn, Freund's complete or incomplete adjuvants, cholera toxin (CT), CTA1-DD, heat-labile enterotoxin (LT), mutants of CT or LT, poly-IC, dendritic cell (DC) binding peptides and C3d fusion proteins.

12. The method according to claim 1, wherein the immunogenic composition is a pan-protective vaccine.

13. The method according to claim 1, wherein the *H. pylori* infection is associated with a gastroduodenal disorder caused by *H. pylori*.

14. The method of claim 13, wherein the gastroduodenal disorder is selected from the group consisting of gastritis, chronic gastritis, gastric or duodenal ulcer, stomach cancer and mucosa associated lymphoid tissue (MALT) lymphoma.

15. The method according to claim 1, wherein the immunogenic composition further comprises one or more pharmaceutically acceptable carriers and/or excipients.

16. The method according to claim 1, wherein the immunogenic composition induces a humoral and/or cell-mediated immune response that is specific to the polypeptide of SEQ ID NO: 1 in the subject.

17. The method according to claim 13, wherein the immunogenic composition induces a T-cell response that is specific to the polypeptide of SEQ ID NO: 1 in the subject.

* * * * *